US009526749B2

(12) United States Patent
Walker et al.

(10) Patent No.: US 9,526,749 B2
(45) Date of Patent: Dec. 27, 2016

(54) METHODS OF ISOLATING DISTINCT PANCREATIC CELL TYPES

(71) Applicant: Yeda Research and Development Co. Ltd., Rehovot (IL)

(72) Inventors: Michael D. Walker, Rehovot (IL); Yoav Soen, Rehovot (IL); Revital Sharivkin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/627,593

(22) Filed: Feb. 20, 2015

(65) Prior Publication Data

US 2015/0157668 A1    Jun. 11, 2015

Related U.S. Application Data

(63) Continuation of application No. PCT/IL2013/050713, filed on Aug. 21, 2013.

(60) Provisional application No. 61/691,826, filed on Aug. 22, 2012.

(51) Int. Cl.
*A61K 35/39* (2015.01)
*C12N 5/071* (2010.01)

(52) U.S. Cl.
CPC ............ *A61K 35/39* (2013.01); *C12N 5/0676* (2013.01); *C12N 2501/415* (2013.01); *C12N 2501/50* (2013.01); *C12N 2501/505* (2013.01); *C12N 2501/585* (2013.01); *C12N 2501/599* (2013.01); *G01N 2500/10* (2013.01)

(58) Field of Classification Search
None
See application file for complete search history.

(56) References Cited

U.S. PATENT DOCUMENTS

| 2006/0205072 | A1* | 9/2006 | Uchida | .............. | C07K 16/2842 |
| | | | | | 435/366 |
| 2007/0072292 | A1 | 3/2007 | Tsang et al. | | |
| 2011/0212067 | A1 | 9/2011 | Karanu et al. | | |

FOREIGN PATENT DOCUMENTS

| WO | WO 2005/021728 | 3/2005 |
| WO | WO 2014/030166 | 2/2014 |

OTHER PUBLICATIONS

International Preliminary Report on Patentability Dated Feb. 24, 2015 From the International Bureau of WIPO Re. Application No. PCT/IL2013/050713.
International Search Report and the Written Opinion Dated Jan. 8, 2014 From the International Searching Authority Re. Application No. PCT/IL2013/050713.
Dorrell et al. "Isolation of Major Pancreatic Cell Types and Long-Term Culture-Initiating Cells Using Novel Human Surface Markers", Stem Cell Research, XP023905548, 1(3): 183-194, Sep. 1, 2008. p. 187-190, Tables 2, 3.
Kaufman et al. "An Extended Antibody Microarray for Surface Profiling Metastatic Melanoma", Journal of Immunological Methods, XP055092614, 358(1-2): 23-34, Available Online Apr. 2, 2010.
Lukowiak et al. "Identificaiton and Purification of Functional Human Beta-Cells by a New Specific Zinc-Fluorescent Probe", the Journal of Histochemistry & Cytochemistry, XP001053775, 49(4): 519-527, Apr. 2001.
Sharivkin et al. "Proteomics-Based Dissection of Human Endoderm Progenitors by Differential Cell Capture on Antibody Array", Molecular & Cellular Proteomics, XP055092596, 11(9): 586-595, May 10, 2012.
Zhou et al. "Surface Antigen Profiling of Colorectal Cancer Using Antibody Microarrays With Fluorescence Multiplexing", Journal of Immunological Methods, XP055054063, 355(1-2): 40-51, Available Online Feb. 13, 2010.
Office Action and Search Report Dated Mar. 10, 2016 From the State Intellectual Property Office of the People's Republic of China Re. Application No. 201380043052 and Its Translation Into English.

* cited by examiner

*Primary Examiner* — Suzanne M Noakes
*Assistant Examiner* — Stephen Chong

(57) ABSTRACT

Methods of isolating distinct specific cell types within mixed populations of cells. Methods of isolating specific cell types among pancreatic cells, particularly from human islets of Langerhans. Markers and combinations thereof for use in methods of isolating insulin producing islet beta cells for treatment of diabetes.

32 Claims, 8 Drawing Sheets

METHODS OF ISOLATING DISTINCT PANCREATIC CELL TYPES

FIELD OF THE INVENTION

The invention relates to methods of isolating specific cell types within mixed populations of cells. Particularly, the invention relates to isolation of distinct cell types among pancreatic cells including insulin producing islet beta cells, for use in treatment of diabetes.

BACKGROUND OF THE INVENTION

Beta cells of the mature functional pancreas regulate metabolic homeostasis by controlled secretion of insulin. Impaired beta cell function and the resulting insufficient secretion of insulin, lead to persistently elevated levels of blood glucose, the hallmark of diabetes.

Type 1 diabetes (T1D, also known as insulin dependent diabetes mellitus, IDDM) is an autoimmune disease that results in the destruction of the beta-cells in the pancreas. The collapse of glucose homeostasis and clinical manifestation of the disease is thought to occur only after 80-90% of pancreatic beta cells have been inactivated by the immune response. Incipient diabetes can be diagnosed by the detection of immunological markers of beta cell autoimmunity only after the onset of the autoimmune process.

Type 2 Diabetes (T2D, formerly non-insulin-dependent diabetes mellitus, NIDDM, or adult-onset diabetes) is the most common form of diabetes, accounting for 90% of cases of diabetes. It is a metabolic disorder that is characterized by high blood glucose in the context of relative insulin resistance and insulin deficiency. Obesity is the primary cause of T2D in people who are genetically predisposed to the disease. Type 2 diabetes is initially managed by increasing exercise and dietary modification. If blood sugars are not lowered by these measures, medications such as metformin or insulin may be needed.

Current treatments for diabetes are problematic and do not eliminate many of the long term complications associated with the disease. Consequently, there is great interest in developing improved treatments for diabetes.

The adult pancreas is composed of endocrine and exocrine cell populations. The endocrine cells are located within the islets of Langerhans, comprising cell-types of discrete functionalities (e.g. alpha cells producing glucagon, beta cells producing insulin, delta cells producing somatostatin etc.). In addition to the heterogeneity of the islets themselves, islet preparations are often contaminated by varying fractions of exocrine cells (including acinar cells, characterized by hydrolytic enzymes e.g. trypsin, chymotrypsin, amylase, lipase; and duct cells (Cleveland et al. 2012)) and even non-pancreatic cells. Pancreatic beta cells regulate metabolic homeostasis by controlled secretion of insulin; impaired beta cell function leads to persistently elevated levels of blood glucose, the hallmark of diabetes. Transplantation of functional pancreatic beta cells is one of the most promising approaches towards curing diabetes (Shapiro et al. 2000, N Engl J Med 343(4): 230-238; Serup et al. 2001, Bmj 322(7277): 29-32), but is currently limited by a severe shortage of donor tissue. This has motivated approaches capable of in vitro generation of functional insulin-producing cells (Kroon et al. 2008, Nat Biotechnol 26(4): 443-452; Russ et al. 2011, PLoS One 6(9): e25566). However, the lack of cell type-specific surface markers is a major obstacle for isolation of relevant cells.

The ongoing world-wide epidemic of diabetes emphasizes the urgent need for improved diabetes treatments such as cell based therapies, hence the enormous interest in hESCs-derived pancreatic precursors. Recent results have demonstrated the potential of hESC-derived precursors to produce insulin in vivo (Kroon et al., Nat Biotechnol. 2008, 26,4, 443-52); yet the protocols are very inefficient and yield highly heterogeneous populations. Therefore, any future clinical use would likely require prospective identification and generation of precursor populations with higher fidelity.

One approach is to generate beta cells in vitro from human embryonic stem cells (hESCs). hESCs are pluripotent cells, capable of generating every cell of the body. Since their initial derivation, hopes have been high that these cells might represent a source of unlimited numbers of beta cells, or beta cell progenitors for transplantation to diabetics. Another potential source is based on in vitro expansion of adult beta cells. Such expansion is accompanied by loss of beta cell markers and requires re-differentiation procedures to restore insulin expression (Russ et al., Diabetes. 2008, 57, 1575-83; Russ et al., PLoS One. 2011, 6, 9, e25566). Another serious impediment to cell replacement therapy is the current lack of cell surface markers selective for pancreatic cell subtypes.

Current methods for identification of cell surface markers are based on flow cytometry, analysis of gene expression patterns and immunostaining. Higher throughput proteomics approaches based on antibody arrays, have also been used for profiling cell surface markers (Ko et al. 2005, Biomaterials 26(23): 4882-4891) and for discriminating cell populations based on differentially expressed markers (Sharivkin et al. Molecular & cellular proteomics 2012, 11(9): 586-595; and Belov et al. Cancer Res. 2001, 61, 4483-4489). Sharivkin et al. and Belov et al. have used antibody array procedures to screen for potential cell type-specific surface markers for human endoderm progenitors and leukemias, respectively. Although these platforms are very efficient for probing cell surface markers, they do not reveal association of specific markers with a particular function.

Beta cell specific surface markers may facilitate identification and characterization of embryonic beta cell progenitors as well as purification of homogeneous insulin-producing cells from cultures derived from hESCs or re-differentiated beta cells. They may also allow isolation of adult beta cells, thus contributing to future diagnostic applications. One cell surface marker which might be selective for human beta cells is TMEM27. While antibodies were recently raised against this antigen (Vats et al. 2012, Diabetologia 55(9): 2407-2416), it is still unclear if they can be used to purify beta cells by flow cytometry or other methods.

A variety of techniques have been previously employed in an attempt to isolate pancreatic beta cells. These include: genetic labeling (Meyer et al., Diabetes. 1998, 47, 1974-1977), Newport green dye labeling (Lukowiak B et al., J Histochem Cytochem. 2001, 49, 519-528), elimination of duct cells (Banerjee and Otonkoski 2009, Diabetologia 52(4): 621-625), and the generation of hybridoma-derived antibodies which can enrich for different endocrine and non-endocrine cell types (Dorrell et al., Stem Cell Res. 2008, 1, 183-194). None of these techniques, however, relies on beta cell-specific surface markers and the isolated cell populations still exhibit an unknown degree of heterogeneity. The same lack of marker information applies to other endocrine subsets in human pancreas (i.e. alpha cells, delta cells etc.).

There is an unmet need for robust screening procedures capable of identifying markers designating cells of desired type or function. Since tissue samples are often limited in quantity and availability, such procedures should permit functional analysis of multiple markers in parallel using small numbers of cells. Specifically, there is an unmet need for isolating insulin-producing beta cells within pancreatic tissue, for diagnostic and therapeutic uses in diabetes and other pancreatic-related disorders.

SUMMARY OF THE INVENTION

The present invention provides methods of isolation of specific populations of cells using newly identified markers and selection means. More specifically, the present invention provides efficient tag-free isolation of pancreatic cell subtypes using specific cell surface markers.

The present invention further provides novel combinations of cell markers suitable for identifying or enriching distinct cells populations, particular distinct cell subtypes within human islets of Langerhans. Uses of the markers and of the isolated cells in diagnosis and treatment of diabetes and other pancreatic disorders are also provided, as well as methods of identifying markers for improvement of purification of beta cells from pancreatic tissue.

Pancreatic beta cell specific surface markers are of particular interest as they may facilitate purification of mature, functional insulin-producing beta cells suitable for transplantation and/or for diagnostic applications. These markers may also be used for isolation of pluripotent or partially differentiated beta cell progenitors which may be used as an abundant source of beta cells for diabetes cell replacement therapy.

It is now disclosed for the first time, using antibody array procedures that certain cell-surface markers, not previously identified in connection with pancreatic cells or with diabetes, are consistently expressed in human islets. These markers were utilized to fractionate distinct cell populations from human islets of Langerhans and to tag-free isolate enriched populations of insulin-producing beta cells from the tissue containing other types of cells.

The present invention thus provides, according to one aspect, a method of isolating an enriched population of at least one distinct type of pancreatic cells from a heterogeneous population of cells, comprising sorting the cells using a combination of at least two cell-surface markers relevant to the cell type to be isolated.

According to some embodiments the heterogeneous population of cells is selected from the group consisting of cells recovered or extracted from pancreatic tissue, committed lineages of stem cells and cultures of differentiated stem cells.

According to various embodiments, the invention provides a method of isolating at least one distinct type of cells, wherein the at least one cell-type is selected from the group consisting of: beta cells (insulin secreting cells), delta cells (somatostatin secreting cells), alpha cells (glucagon secreting cells) and exocrine cells (trypsin secreting cells). Each possibility represents a separate embodiment of the invention.

According to some specific embodiments, the invention provides methods of isolating beta cells or beta cell progenitors.

The present invention provides, according to some embodiments, a method of isolating an enriched population of at least one distinct type of pancreatic cells from a heterogeneous population of cells selected from the group consisting of cells recovered or extracted from pancreatic tissue, committed lineages of stem cells and cultures of differentiated stem cells, comprising sorting the cells using a combination of at least two cell-surface markers relevant to the cell type to be isolated, wherein the at least one distinct type of cells is selected from the group consisting of: beta cells and delta cells, and wherein one cell-surface marker is CD9.

According to some embodiments, the at least one distinct type of cells is selected from the group consisting of: beta cells and delta cells, and wherein a first cell marker is CD9.

According to some embodiments, the beta cells are enriched for using positive sorting or selection with the cell-surface marker CD9 (NP_001760.1, human species).

According to some embodiments, the cell surface marker CD9 is the first marker used for selection.

According to some embodiments, the beta cells are enriched for using positive selection with a combination of the cell-surface markers CD9 and CD56.

According to a specific embodiment, the CD56 is NP_000606.3.

According to yet other embodiments, the beta cells are isolated using a combination of the cell-surface markers CD9 and EGFR, wherein CD9 is used for positive selection and EGFR is used for negative selection.

According to some embodiments, the EGFR cells surface is NP_005219.2.

According to yet other embodiments, the beta cells are isolated using positive selections with combination of the cell-surface markers CD9 and CD56 and further selection with at least one additional cell-surface marker.

According to some embodiments, the at least one additional cell-surface marker is selected from the group consisting of: CD4, CD73, CD87, CCR4, CD165, CD85J, CD221, CD153 (CD30L), CD142, CD134, ITGB7, CD68, WNT16, CD18, CD6, CD77, CD61, and CD32. Each possibility represents a separate embodiment of the invention.

According to some embodiments, at least one additional cell-surface marker is selected from the group consisting of: CD4 (NP_000607.1), CD73 (NP_001191742.1, CD87 (NP_002650.1), CCR4 (NP_005499.1), CD165 (Gene ID 23449), CD85J (NP_001075106.1), CD221 (NP_000866.1), CD153 (CD30L) (NP_001235.1), CD142 (NP_001171567.1), CD134 (NP_003318.1), ITGB7 (NP_000880.1), CD68 (NP_001035148.1), WNT16 (NP_057171.2), CD18 (NP_000202.2), CD6 (NP_001241679.1), CD77 (NP_059132.1), CD61 (NP_000203.2), and CD32 (NP_001002273.1). Each possibility represents a separate embodiment of the invention.

According to yet other embodiments, the beta cells are isolated using a combination of at least two cell-surface markers wherein one marker is CD9 and at least one other marker is selected from the group consisting of: CD56 (NP_000606.3), EGFR (NP_005219.2), CD4 (NP_000607.1), CD73 (NP_001191742.1, CD87 (NP_002650.1), CCR4 (NP_005499.1), CD165 (Gene ID 23449), CD85J (NP_001075106.1), CD221 (NP_000866.1), CD153 (CD30L) (NP_001235.1), CD142 (NP_001171567.1), CD134 (NP_003318.1), ITGB7 (NP_000880.1), CD68 (NP_001035148.1), WNT16 (NP_057171.2), CD18 (NP_000202.2), CD6 (NP_001241679.1), CD77 (NP_059132.1), CD61 (NP_000203.2), and CD32 (NP_001002273.1). Each possibility represents a separate embodiment of the invention.

According to some embodiments, the isolated beta cells are mature, functional insulin-producing cells.

According to some embodiments, the beta cells are isolated from extracts of human islets of Langerhans.

According to some embodiments, beta cells are isolated from committed lineages of stem cells and cultures of differentiated stem cells According to yet other embodiments, beta cells or beta cell progenitors are isolated from cultures derived from human stem cells.

According to some embodiments beta cells or beta cell progenitors are isolated from populations of human induced pluripotent stem cells.

According to other embodiments beta cells or beta cell progenitors are isolated from human adult stem cells.

According to yet other embodiments, beta cells or beta cell progenitors are isolated from human embryonic stem cells obtained by methods that that do not involve the destruction of embryos.

According to other embodiments, isolated cells are selected from the group consisting of: insulin-secreting cells, somatostatin-secreting cells, trypsin-secreting cells and glucagon secreting cells.

According to some embodiments, a method for isolating glucagon-producing alpha cells is disclosed comprising using a combination of the cell surface markers CD9 and CD56 wherein the CD9 marker is used for negative selection and the CD56 is used for positive selection.

According to other embodiments, a method for isolating trypsin-producing acinar cells is disclosed comprising using a combination of the cell surface markers CD9 and CD56, wherein both markers are used for negative selection.

According to a specific embodiment the method of isolating an enriched population of at least one distinct type of pancreatic cells from a heterogeneous population of cells comprises the steps:
  i. obtaining a heterogeneous population of cells selected from the group consisting of cells recovered or extracted from pancreatic tissue, committed lineages of stem cells and cultures of differentiated stem cells;
  ii. exposing the cells obtained in (i) to a probe capable of identifying CD9+ cells and to at least one additional probe;
  iii. isolating cells expressing CD9 and the additional probe by sorting of cells, thereby isolating an enriched population of at least one distinct cell type selected from the group consisting of: beta cells and delta cells.

According to some embodiments, the at least one additional probe is selected from the group consisting of: CD 56, CD4, CD73, CD87, CCR4, CD165, CD85J, CD221, CD153 (CD30L), CD142, CD134, ITGB7, CD68, WNT16, CD18, CD6, CD77, CD61, and CD32. Each possibility represents a separate embodiment of the invention.

According to some embodiments, the at least one additional probe is selected from the group consisting of: CD56 (NP_000606.3), CD4 (NP_000607.1), CD73 (NP_001191742.1, CD87 (NP_002650.1), CCR4 (NP_005499.1), CD165 (Gene ID 23449), CD85J (NP_001075106.1), CD221 (NP_000866.1), CD153 (CD30L) (NP_001235.1), CD142 (NP_001171567.1), CD134 (NP_003318.1), ITGB7 (NP_000880.1), CD68 (NP_001035148.1), WNT16 (NP_057171.2), CD18 (NP_000202.2), CD6 (NP_001241679.1), CD77 (NP_059132.1), CD61 (NP_000203.2), and CD32 (NP_001002273.1). Each possibility represents a separate embodiment of the invention.

According to a specific embodiment, the at least one additional probe is CD56 used for positive selection of cells.

According to another specific embodiment, the at least one additional probe is Epidermal Growth Factor Receptor (EGFR), used for negative selection of cells.

According to some embodiments, the EGFR is NP_005219.2, NP_958439.1, NP_958440.1, or NP_958441.1. Each possibility represents a separate embodiment of the invention.

According to some embodiments, purified cells of iii are subject to additional iterations comprising steps (ii)-(iii) with additional probes used for positive or negative selection of cells.

According to some embodiments, the sorting methodology is fluorescence activated cell sorting (FACS).

According to some embodiments, the distinct cell types are isolated from human pancreatic tissue.

According to a specific embodiment, the cells are isolated from human islets of Langerhans.

According to some embodiments, at least one cell-surface marker is used for positive or negative sorting of cells according to any of the methods described above, for isolating at least one distinct cell type of cells from human islets of Langerhans, wherein the at least one cell-surface marker is selected from the group consisting of: CD104, (Integrin, beta 4: AAI43739.1); CD11A, (integrin alpha-L isoform b precursor: NP_001107852.1); CD11B/MAC1, (integrin alpha-M isoform 2: NP_000623.2); CD11C, (integrin alpha-X: NP_000878.2); CD135, (Fms-related tyrosine kinase 3: AAI44041.1); CD140B, (Platelet-derived growth factor receptor, beta polypeptide: AAH32224.1); CD142, (Coagulation factor III/thromboplastin, tissue factor: AAH11029.1); CD146, (cell surface glycoprotein MUC18: NP_006491.2); CD147, (basigin: NP_940992.1); CD15, (alpha-(1,3)-fucosyltransferase: NP_002024.1); CD164, (CD164 antigen, sialomucin, isoform CRA_: EAW48353.1); CD166, (Activated leukocyte cell adhesion molecule: AAI37097.1); CD177, (glycoprotein NB1: CAC83758.1); CD197, (C-C chemokine receptor type 7: NP_001829.1); CD221 3b7, (insulin-like growth factor 1 receptor: NP_000866.1); CD226, (T-cell immunoreceptor with Ig and ITIM: NP_776160.2); CD271, (tumor necrosis factor receptor superfamily member 16: NP_002498.1); CD28, (T-cell-specific surface glycoprotein isoform 2: NP_001230006.1); CD282, (toll-like receptor 2: NP_003255.2); CD29, (integrin beta-1 isoform 1A: NP_002202.2); CD3, (T-cell surface glycoprotein CD3 gamma chain: NP_000064.1); CD36, (antigen CD36: AAA58413.1); CD42B, (platelet glycoprotein 1b alpha chain: NP_000164.5); CD44, (cell surface glycoprotein CD44: AAB13625.1); CD45RB (interleukin-27 subunit alpha precursor: NP_663634.2); CD47, (leukocyte surface antigen CD47 isoform 2: NP_942088.1); CD49B, (integrin alpha-2: NP_002194.2); CD49E, (integrin, alpha 5/fibronectin receptor, alpha polypeptide: AAH08786.1); CD49F, (Integrin, alpha 6: AAI36457.1); CD50, (Intercellular adhesion molecule 3: AAH58903.1); CD53, (leukocyte surface antigen CD53: NP_000551.1); CD54, (Intercellular adhesion molecule 1: AAH15969.1); CD55, (CD55 antigen, decay accelerating factor for complement/Cromer blood group, isoform CRA_j: EAW93497.1); CD57, (galactosylgalactosylxylosylprotein 3-beta-glucuronosyltransferase 1: NP_061114.2); CD59, (CD59 glycoprotein: NP_976076.1); CD61, (Integrin, beta 3/platelet glycoprotein IIIa, antigen CD61: AAI27668.1); CD63, (CD63 antigen isoform A: NP_001244320.1); CD66, (integrin beta-2: NP_000202.2); CD66B, (Carcinoembryonic antigen-related cell adhesion molecule 8: AAH26263.1); CD66C, (Carcinoembryonic antigen-related cell adhesion molecule 6: AAH05008.1); CD71, (transferrin receptor protein 1: NP_001121620.1); CD81, (CD81 antigen/target of antiproliferative antibody 1: EAX02508.1); CD9, (CD9 antigen: NP_001760.1); CD90, (Thy-1 cell surface antigen: AAH65559.1); CD97, (CD97 antigen, isoform CRA_b: EAW84413.1); CD98, 4F2 (cell-surface antigen heavy chain isoform c: NP_002385.3); CD99, (CD99 antigen isoform X24: XP_005274856.1); C-ERB-2, (protooncogene protein: AAA35808.1); CLIP, (CAP-Gly domain-containing linker protein 1 isoform a: NP_002947.1); CXCR4, (C-X-C chemokine receptor type 4 isoform a: NP_001008540.1); EGFR, (epidermal growth factor receptor variant A: ADL28125.1); HLA-A2, (MHC class I antigen HLA-A2: AAA87076.1); HLA-ABC, (MHC class I antigen, partial: AAA59602.1); HLA-DR, (MHC class II antigen: ADM15723.1); Hematopoietic progenitor cell, (KS1/4, epithelial cell adhesion: NP_002345.2); LTBR, (lymphotoxin beta receptor/TNFR superfamily, member 3: EAW88802.1); P-Glycoprotein: AAA59575.1; SCARB1, (scavenger receptor class B member 1: NP_005496.4); TROP-2 (integrin beta-1 isoform 1A: NP_596867.1); B2-microglobulin: AAA51811.1. Variants of said cell-surface markers, having different accession numbers are also included in the scope of the present invention. Each possibility represents a separate embodiment of the invention.

According to some embodiments, the distinct cell-types are selected from the group consisting of: beta cells, delta cells, alpha cells and exocrine cells. Each possibility represents a separate embodiment of the invention.

According to some embodiments the distinct cell type is beta cells or beta cell progenitors.

Uses of the isolated cells for diagnosis and therapy, as well as for research, are also within the scope of the present invention.

According to some embodiments, beta cells or beta cell progenitors, isolated according to the present invention are used for transplantation to a mammalian subject for prevention or treatment of diabetes.

According to some embodiments, mature, functional insulin-producing beta cells, isolated according to the present invention are used for transplantation.

According to other embodiments, beta cell progenitors, isolated from cultures derived from hESCs or re-differentiated beta cells, are used for transplantation.

According to some embodiments, the mammalian subject is a human subject.

A method of prevention or treatment of diabetes is also disclosed, comprising transplantation of to a mammalian subject in need thereof a population of beta cells or beta cell progenitors isolated according to the methods of the present invention.

According to some embodiments the mammalian subject is a human subject.

According to some embodiments the population of beta cells comprises mature, functional insulin-producing beta cells.

According to other embodiments, the beta cell progenitors were isolated from culture derived from hESCs or re-differentiated beta cells.

According to other embodiments, the isolated cells are used for diagnostic applications or for development of diagnostic tools.

According to some embodiments isolated cells according to the present invention are used to quantify the number and state of beta cells in subjects in need thereof, thus allowing detection of diabetes prior to the onset of hyperglycemia symptoms.

According to other embodiments, embryonic stem cells or partially differentiated stem cells or beta cell progenitors isolated according to the present invention are used as a source of beta cells for diabetes cell replacement therapy.

According to some embodiments, said embryonic stem cells comprise human cells obtained only by methods that that do not involve the destruction of embryos.

According to yet other embodiments, isolated beta cells are used in research to study differentiation pathways that leads embryonic stem cells to become insulin-producing beta cells.

The present invention also provides a functional screening method for identifying cell-surface marker combinations suitable of purifying or enriching a population of cells within heterogeneous populations of cells, the method comprises the steps of:
  i. obtaining a heterogeneous population of cells;
  ii. applying the heterogeneous cells of (i) to an array comprising antibodies against cell-surface markers, to allow binding of cells to the array;
  iii. immunostaining the bound cells of (ii) with antibodies specific for a functional marker thereby identifying antibody stained loci enriched for functional cells; and
  iv. determining the cell-surface markers at the loci enriched for the functional cells of (iii).

According to some embodiments, the method comprises fixing and permeabilizing the cells before immunostaining of (iii).

According to some embodiments, cells obtained in (i) are isolated based on a relevant marker, before performing step (ii).

According to some specific embodiments, isolation is performed by fluorescence activated cell sorting (FACS).

According to some embodiments, marker combination is used for improving the degree of purity of cell isolation or for fractionation of heterogeneous cellular systems.

According to some embodiments the functional screening method is used for identifying cell-surface marker combinations suitable of purifying enriched population of insulin-producing beta cells within pancreatic tissue, wherein the method comprises the following steps:
  i. obtaining a heterologous population of cells selected from the group consisting of cells recovered or extracted from pancreatic tissue, committed lineages of stem cells and cultures of differentiated stem cells;
  ii. isolating CD9+ cells from the cells obtained in (i);
  iii. applying the CD9+ cells of (ii) to an array comprising antibodies against cell-surface markers;
  iv. immunostaining the bound cells of (iii) with antibodies against insulin and somatostatin thereby identifying antibody stained loci enriched for beta and delta cells; and
  v. determining the cell-surface markers of the loci enriched for beta cells in (iv).

According to other embodiments, the functional screening method is used for identifying cell-surface markers suitable of purifying enriched populations of cells selected from the group consisting of: pancreatic exocrine cells, pancreatic endocrine cells such as beta cells, alpha cells and non-pancreatic cells such as blood cells.

According to some specific embodiments, the functional screening method is used for identifying further cell-surface markers suitable of purifying enriched populations of cells selected from the group consisting of: insulin-secreting cells, somatostatin-secreting cells, trypsin-secreting cells and glucagon secreting cells. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
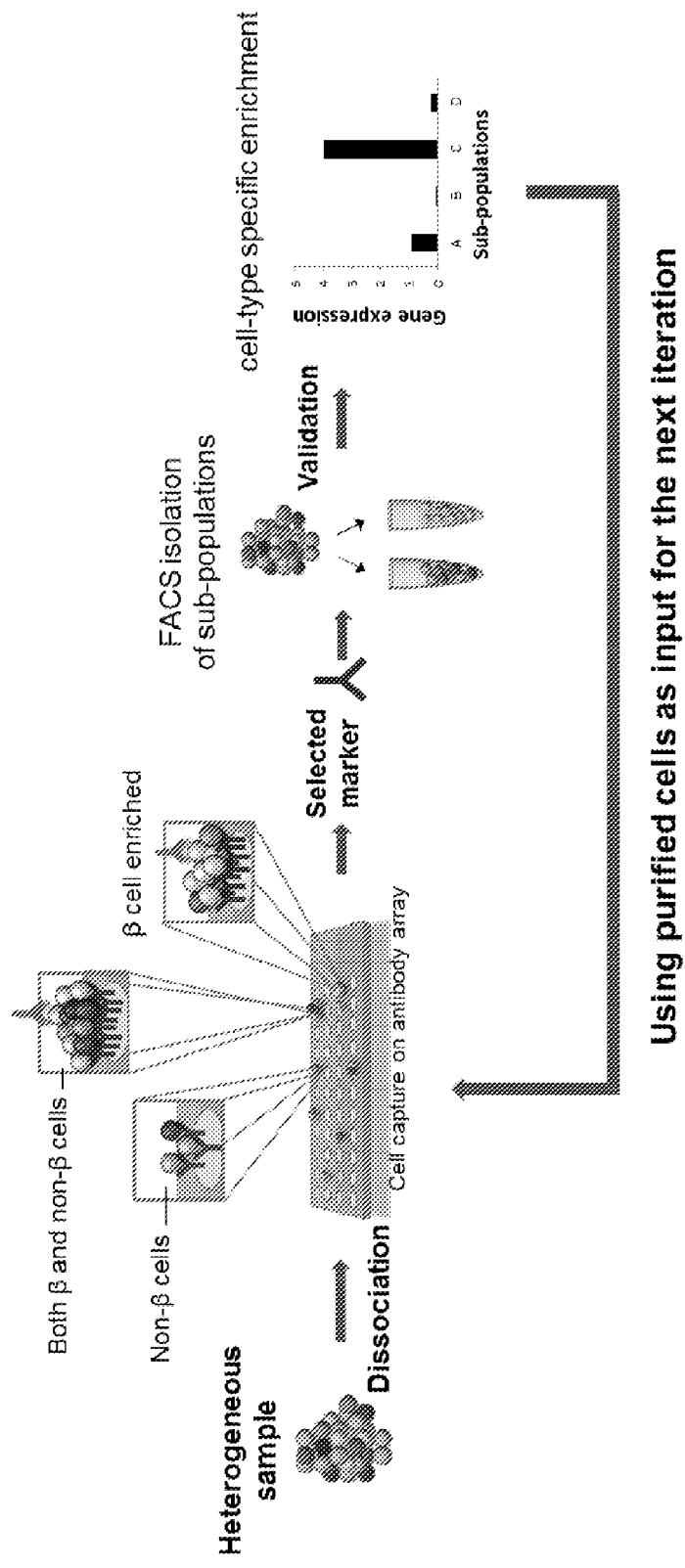
FIG. 1A: Schematic presentation of the iterative high throughput screening assay—the functional cell-capture screen (FCCS) approach. An array of antibodies against cell-surface antigens is printed on a hydrogel coated glass slide. Live cells in suspension are captured on specific antibody spots by interaction between their surface antigens and the printed antibodies. The captured cells are fixed and labeled for one or more intracellular markers of functional relevance (e.g. insulin, glucagon, somatostatin for pancreatic beta, alpha and delta cells, respectively). Populated spots enriched by cells with the desired label designate markers that are preferentially associated with respective cell functionality. Following validation of the marker, it is used to isolate cells by flow cytometry. The isolated cells are then used as an input sample for the next iteration of this procedure. The iterative application of the procedure allows identification of additional markers that further refine the isolation.

An iterative high throughput screen which identifies and associates cell surface markers with a functional, cell-specific property such as insulin production is provided. The technique, termed functional cell-capture screen (FCCS), is compatible with screening many surface markers for multiple functionalities in limited and heterogeneous samples. The efficiency and specificity of this approach is herein demonstrated by identifying novel markers enriching for beta, alpha, delta and acinar cells from cadaveric samples of human pancreatic islets of Langerhans.

Cell replacement therapy using insulin-producing cells is considered a promising approach for treatment of diabetes. However, like many other research and medical applications, it is seriously limited by the lack of selective cell surface markers for tag-free isolation of desired cells from heterogeneous samples. The present invention addresses this problem using a novel proteomics procedure. It detects and associates specific cell surface markers with particular cell functionality by coupling cell capture on antibody arrays with immunofluorescent labeling. Using this approach in an iterative manner, marker combinations enriching for discrete pancreatic cell subtypes were discovered from preparations of human islets of Langerhans: insulin-producing beta cells ($CD9^{high}$/CD56+), glucagon-producing alpha cells (CD9−/CD56+) and trypsin-producing acinar cells (CD9−/CD56−). This strategy may allow isolation of clinically relevant cells for treatment of diabetes. It is also generally applicable to function-based purification of desired cell types from other heterogeneous cellular systems.

Pancreatic beta cell specific surface markers are of particular interest as they may facilitate purification of mature, functional insulin-producing beta cells suitable for transplantation and/or for diagnostic applications. These markers may also be used for isolation of embryonic or partially differentiated beta cell progenitors which may be used as an abundant source of beta cells for diabetes cell replacement therapy.

Suitably, said embryonic cells or partially differentiated cell progenitors comprise human cells obtained only by methods that that do not involve the destruction of embryos. Such methods were described, for example by Chung et al., Cell Stem Cell, 2008, 2(2), 113-117.

Specific combinations of cell-surface markers were identified and utilized for the first time in the present invention for isolating distinct cell-types, particularly beta cells, within pancreatic tissue.

The relevant markers and combinations thereof where identified by screening human islets of Langerhans using cell sorting methods and novel functional screening assay.

The new assay disclosed herein may be further used to identify additional cell-surface markers suitable of isolating distinct cell populations of interest.

It was shown for the first time that tag-free isolation based on the CD9+/CD56+ marker combination yielded highly enriched beta cell population, and that use of or addition of other identified markers to the isolation process could improve the purity of the obtained population of cells. It is further shown that other combinations of markers are suitable of isolating other types of cells e.g. delta, alpha or exocrine cells.

An antibody array platform was used to characterize the cell-surface marker profile of human pancreatic islets. Despite differences in donor age, gender, and BMI and unlike the highly variable qPCR measurements of mRNA expression in different donors, this approach proved to be reproducible and efficient. Potential candidate markers from the list of reproducible markers allowed isolation of exocrine (CD44, CD49B, EGFR) and endocrine (CD9) fractions of the sample. Sorting of cells based on the labels of both CD9 (positive) and EGFR (negative) provided an unprecedented enrichment of specific islet cell subtypes. The ability to further refine sub-fractionation of each compartment and increase the enrichment of desired cells is greatly advanced by the first described functional screening assay. It solves two major problems simultaneously: (1) it allows screening of hundreds of cell surface markers using small sample sizes ($2\times10^5$ cells), and (2) it enables direct association between cell surface markers and a desired property (e.g. expression of insulin, somatostatin, glucagon, etc.). These experiments identified additional marker combinations that are likely to further improve the degree of purity of cell isolation. The same approach can be generally applied for numerous other cases of cell fractionation of heterogeneous cellular systems. For example, re-differentiated beta cells (BCDs) and cells derived from endometrium biopsies can be separated using the approach of the present invention.

The selective markers and procedures described for the first time in the present invention, may contribute to the effort for utilizing hESCs-derived pancreatic precursors by providing efficient means to purify both precursors and mature beta cells from a variety of potential sources (e.g. pluripotent stem cells and more differentiated, patient-derived cells). Eventually, it may help the derivation of clinically pure precursors for transplantation and contribute to future diagnostic applications.

The association of a functional readout with cell capture on the array represents a new strategy to identify functionally relevant markers among the majority of other markers. This strategy solves two major problems simultaneously: (1) It enables screening of hundreds of cell surface markers using small sample sizes (~$4\times10^5$ cells), and (2) it provides direct association between cell surface markers and a desired functional attribute (e.g. expression of insulin, somatostatin, glucagon, etc.). Currently, it is the most efficient way to perform a cell-type specific high-throughput screen in heterogeneous samples of limited size. The efficiency and specificity of the approach was demonstrated by identifying markers for purification of distinct pancreatic cell types within samples of human islets of Langerhans. This approach produced reproducible results despite differences in donor age, gender, and BMI.

In more details, the data presented herein for the first time showed that different combinations of CD9 and CD56 enrich for different pancreatic cell types. CD9high/CD56+ enriched for beta and delta cells, CD9−/CD56+ for alpha cells and CD9−/CD56− enriched for acinar cells. This is a novel procedure for isolation of live human pancreatic beta or alpha cells using defined endogenous markers. Quantitative assessment of the purity and yield of isolated cells requires analysis of co-expression with lineage-specific genes at single cell resolution. This was achieved by combining intracellular FACS for insulin with standard FACS analysis of co-expression of either CD9 or CD9/CD56. It was shown previously (Banerjee and Otonkoski 2009 ibid), that CD56 (NCAM, or sialylated CD56), was not useful as a single marker for purification of insulin+ cells. On the other hand, the combination of CD9/CD56, demonstrated for the first time in the present invention, produced effective beta cell purification. Indeed, the CD9/CD56 combination produced higher beta cell purity compared to single CD9-based isolation. Improved purity often comes at the expense of yield. Consequently, addition of a second marker for isolation tends to restrict the selection, resulting in reduced yield. Nevertheless, the iterative use of the FCCS allowed us to identify a combination of markers (CD9 and CD56) which increased the purity without compromising the yield.

As demonstrated in previous studies (Dorrell et al. 2008 ibid), the enrichment of beta cells coincided with enrichment of delta cells. This is consistent with the developmental proximity between these cell types; indeed, the divergence of beta and delta cells is one of the last specification events of endocrine tissue in the embryo, perhaps leading to higher similarity between beta and delta cells as compared to other endocrine lineages. Discriminating beta from delta cells is therefore more difficult and may be achieved by additional iterations of the FCCS with co-staining for insulin and somatostatin.

The terms "isolating" and "isolation" according to the present invention encompass not only selecting a pure population of specific cell type but also selecting a cell population that is enriched in cells of a specific type.

Enrichment according to the present invention refers to improving the purity of a cell population. According to some embodiments enriched population of cells comprises at least 50% of the cells of interest. According to other embodiments the enriched population of cells comprises at least 60%, 70%, 80%, 90% or 95% of the cells of interest. Each possibility represents a separate embodiment of the invention.

Committed lineages of stem cells according to the present invention refer to the step in differentiation of hESCs into pancreatic beta cells by which the initially pluripotent cell gradually becomes more committed towards the final cell fate of a functional insulin-producing cell. Initially, the pluripotent stem cells differentiate via mesendoderm into definitive endoderm. The definitive endoderm then commits towards a pancreatic cell fate, and these cells in turn differentiate towards an endocrine pancreatic cell fate, after which they commit to beta cells. According to some embodiments the hESCs are obtained by methods that that do not involve the destruction of embryos.

Selecting according to the present invention refers to the process of distinguishing between the cells of interest and at least one other type of cells. The selecting process thus leads to enriching of cells of interest.

As used herein, the phrase "heterogeneous population of cells" refers to mixture of at least two types of cells, one type being the cells of interest for isolation. The heterogeneous population of cells may be derived from any organism or organisms, preferably mammalian and even more preferably human.

The term "cell-surface marker relevant to the cells" denotes a marker which can be used for enrichment of a cell population from a heterogeneous population of cells, either by positive selection (selecting cells expressing said marker) or by negative selection (excluding cells expressing this marker).

Cell markers are identified in the present application by at least one representative accession number of human species. It should be noted however that other human and non-human variants of the cell markers, having different accession numbers may be used in the methods of the present invention.

While demonstrated usefulness for human islet-based research, the approach provided by the present invention could be extended to any cellular context for which a functional readout is available (e.g. labeled metabolites, granulation, ion content, mitotic state etc.). The FCCS may therefore constitute a general and efficient platform for resolving heterogeneous cellular systems.

General Methods
Separation Methods:

Separation of the cells may be performed, in addition to, or in combination with the novel separation methods of the present invention, according to various physical properties, such as fluorescent properties or other optical properties, magnetic properties, density, electrical properties, etc. Cell types can be isolated by a variety of means including fluorescence activated cell sorting (FACS), protein-conjugated magnetic bead separation, morphologic criteria, specific gene expression patterns (using RT-PCR), or specific antibody staining.

The use of separation techniques include, but are not limited to, those based on differences in physical (density gradient centrifugation and counter-flow centrifugal elutriation), cell surface (lectin and antibody affinity), propidium iodide (PI) staining and vital staining properties (mitochondria-binding dye rho123 and DNA-binding dye Hoechst 33342).

Various techniques can be employed to separate the cells. Monoclonal antibodies are particularly useful. The antibodies can be attached to a solid support to allow for separation. The separation techniques employed should maximize the retention of viability of the fraction to be collected.

Various techniques of different efficacy may be employed to obtain "relatively crude" separations. Such separations are where up to 30%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique.

Techniques providing accurate separation include fluorescence activated cell sorters, which can have varying degrees of sophistication, e.g., a plurality of color channels, low angle and obtuse light scattering detecting channels, impedance channels, etc. Other techniques for positive selection may be employed, which permit accurate separation, such as affinity columns, and the like.

Antibodies used for separation may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

Fluorescence Activated Cell Sorting (FACS) Methods:

FACS is typically performed using any of the methods reviewed by Hoeppener et al., Recent Results Cancer Res. 2012, 195, 43-58.

Methods of Culturing Beta Cells:

Beta cells can be maintained and cultured using several methods known in the art. For example Efrat S. (Rev Diabet Stud. 2008, 5, 2, 116-22), describes a method of growing islets in a monolayer for the purpose of expansion. In another method, which allows retention of initial gene expression but does not allow cellular expansion, beta cells are grown in suspension in their spherical structure using the same condition as described above. Typically, islets samples were grown in suspension in their spherical structure using the condition described in—Efrat S. 2008 ibid. This method allows retention of initial gene expression but does not allow cellular expansion.

Methods of Differentiation of Stem Cells into Beta Cells:

Methods for inducing differentiation of pancreatic stem cells into beta cells are known in the art. For example, US 2003/0109036 discloses a method differentiating pancreatic islet stem cells or islet precursor cells into functioning beta cells to treat diabetes mellitus by transplanting the cells into a diabetic animal. Pancreatic cells are isolated and cultured such that the population of nestin-positive cells increases. The cells are then cultured on poly-D-lysine such that cell aggregates form. The cell aggregates are transplanted into a diabetic animal, where they produce insulin and lower blood glucose concentrations. US 2003/0032183 discloses treatment of stem cells with a retinoid induces differentiation of the stem cells into hepaticopancreatic tissue.

US 2003/0077259 provides methods for inducing insulin gene expression in cultured pancreas cells, comprising contacting a culture of endocrine pancreas cells expressing a PDX-1 gene and a NeuroD/BETA2 gene with a GLP-1 receptor agonist, wherein the cells have been cultured under conditions such that the cells are in contact with other cells in the culture, thereby inducing insulin gene expression in the cells.

Additional protocols for embryonic stem cell differentiation towards pancreatic islets are described for example in: Kroon et al., Nat Biotechnol. 2008, 26, 4, 443-52 and Johannesson et al., PLoS One. 2009, 4, 3, e4794.

Beta-islets cells differentiation is identified by the expression of insulin and optionally expression of transcription factors involved in beta-cell development (e.g. Beta2/NeuroD, Nkx6.1 and Is11), at the protein and mRNA levels. Alternative regimens for beta-islet differentiation are described in the art (for example that D'Amour et al., Nature Biotechnologty 2006, 24, 11, 1392-1401, 2006.

Methods of Transplanting Beta Cells:

Beta cells can be transplanted using any method known in the art. For example, islet transplantation in seven patients with type 1 diabetes mellitus using a glucocorticoid-free immunosuppressive regimen was described in Shapiro Et al., N Engl J Med. 2000, 343, 4, 230-8.

Cell Culture:

Human islets were provided through the ECIT Islet for Basic Research program (JDRF award 31-2008-416). Experiments were approved by the Weizmann Institute of Science Bioethics Committee. Samples of islets cells were incubated for 48 hours in suspension (90 mm culture dish, Miniplast, Ein Shemer, 20090-01) in human islets medium: CMRL 1066 (Biological industries, 01-821-1A), 5.6 mM glucose, 10% FBS (Biological Industries, 04-007-1A), 1% PEN-STREP-AMPHO (Biological Industries, 03-033-1B).

Antibody Array:

Antibody array screenings were performed using the procedure described in Sharvikin et al. ibid. Arrays were printed in a Microgrid printer with solid pins (Total array Systems, BioRobotics) on hydrogel coated slides (Full Moon Biosystems) using a panel of 231 monoclonal mouse anti-human antibodies (BD biosciences). Antibodies of human cell-surface markers were printed at a concentration of 0.5 mg/ml in five spots, each using a single stamp and with 750 µm spacing. Following printing, the arrays were hydrated in a humidifier at 4° C. for 48 hours, and then dried for 10 minutes at room temperature.

Figure 1C:
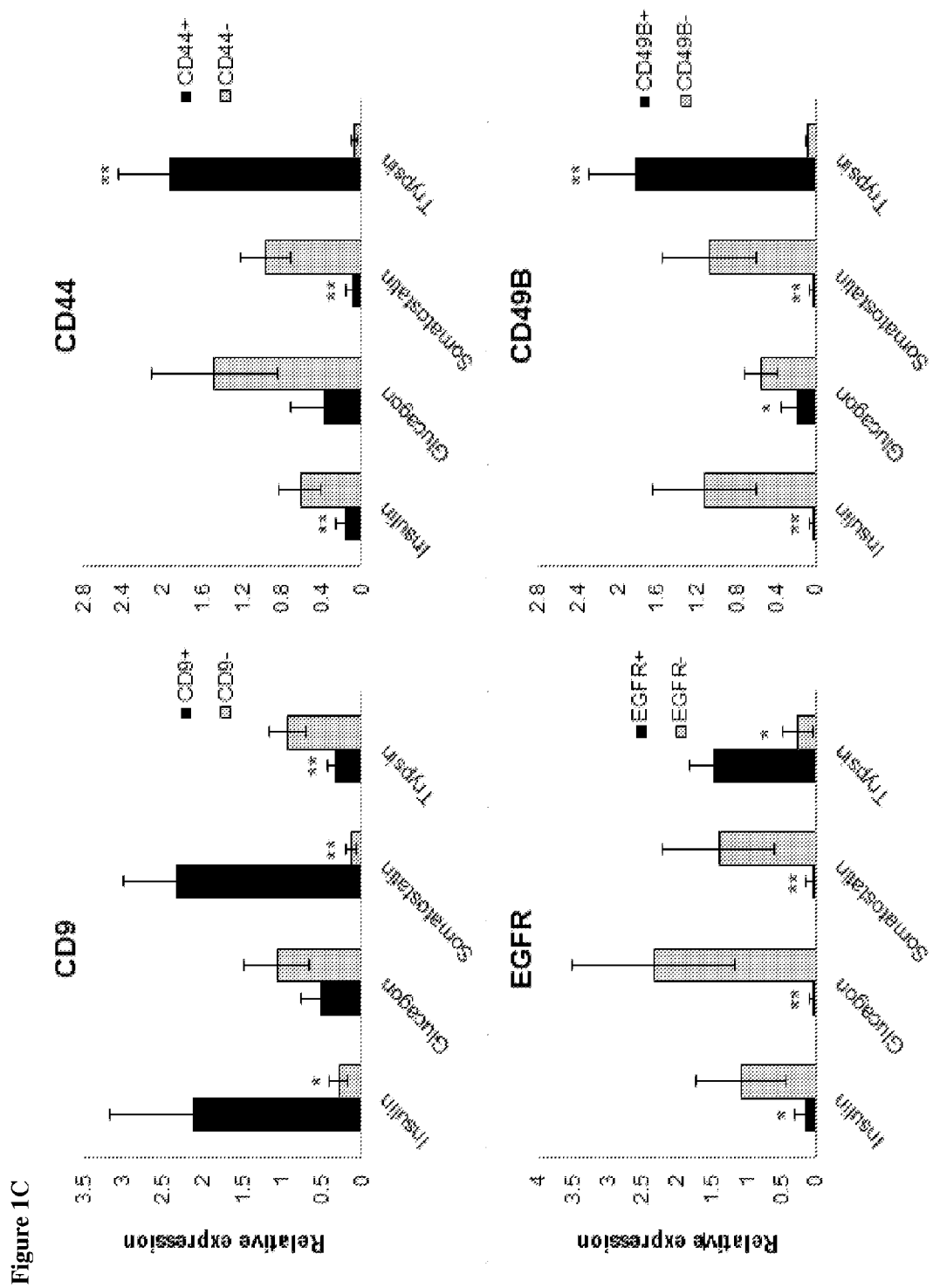
FIG. 1C: Real-time qPCR analysis of several cell-type specific genes in different marker-isolated populations (insulin for beta cells, glucagon for alpha cells, somatostatin for delta cells and trypsin for acinar cells). Shown is mean expression relative to unsorted (bulk) cells+/−SE (n=3; biological replicates correspond to different donors; *p<0.05, **p<0.01).
Figure 2A:
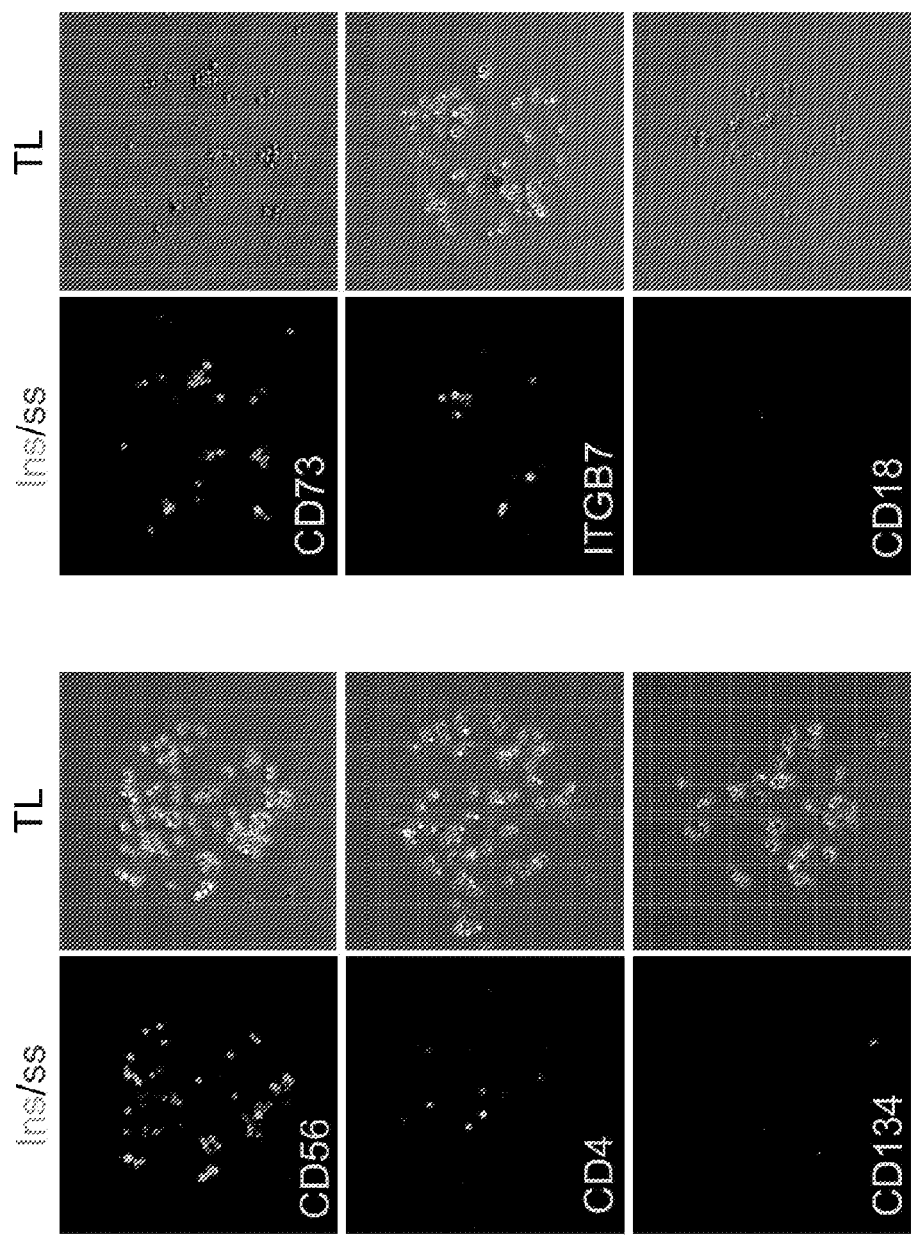
FIG. 2A: Second iteration of FCCS identifies candidate marker combinations for improving the isolation of insulin producing cells. Representative images of spots containing $CD9^{high}$ cells immunostained for insulin and somatostatin. Spots with high, medium and low beta cell enrichment are presented from top to bottom. Respective phase contrast images are shown to the right. 10× magnification.
Figure 2B:
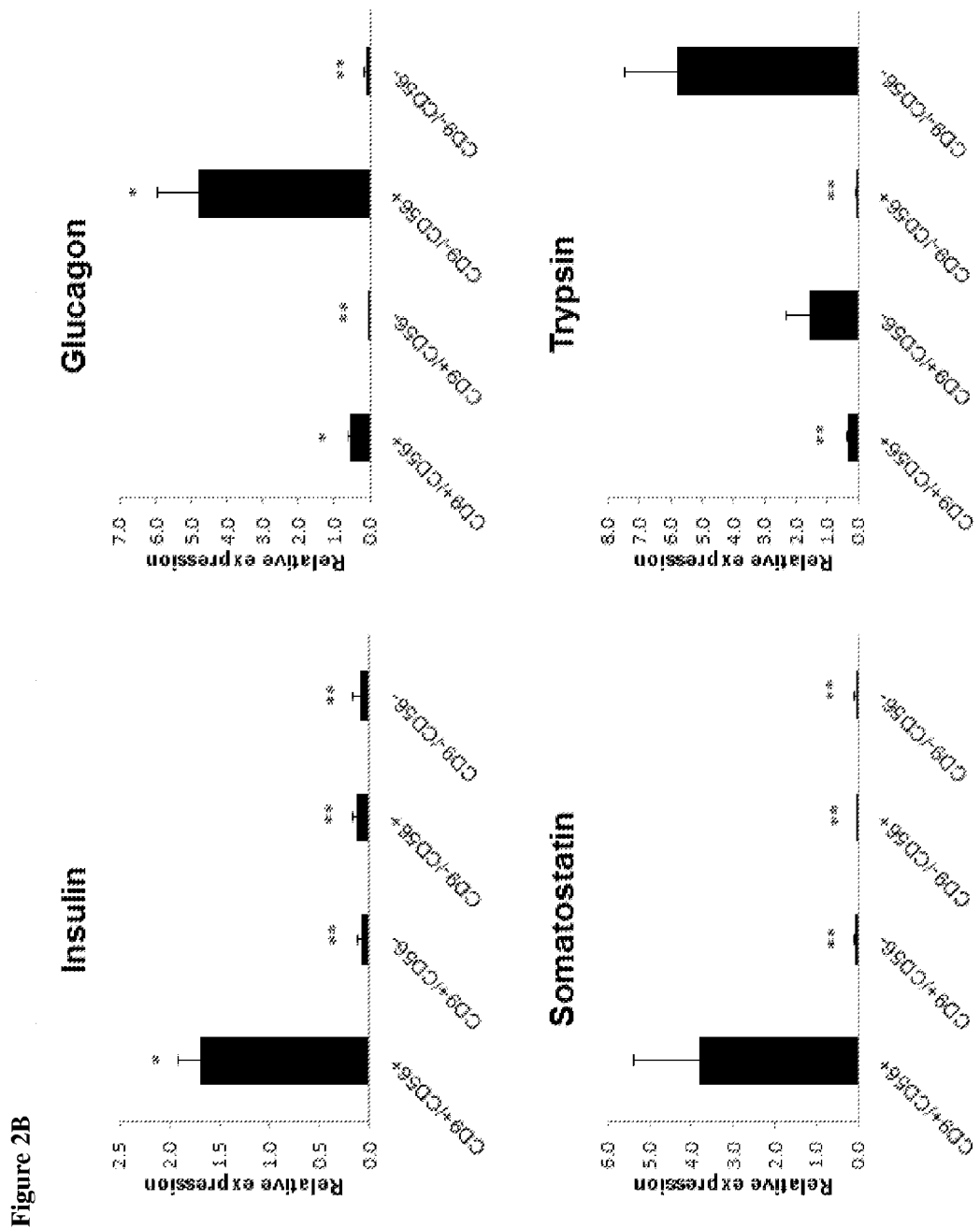
FIG. 2B: qPCR analysis of cell-type specific genes in islet cells fractionated based on CD9/CD56 combinations ($CD9^{high}$/CD56+, $CD9^{high}$/CD56−, CD9−/CD56+ and CD9−/CD56). Shown is mean expression relative to unsorted (bulk) cells+/−SE (n=3; biological replicates correspond to different donors; *p<0.05, **p<0.01).

The FCCS Procedure:

Cells were dissociated using TrypLE™ Express (Invitrogen 12604) for 4 min, followed by quenching with 10% FBS in PBS. They were then seeded on the array at a total concentration of ~5*106 cells/ml in 250-500 µl of human islets medium, supplemented with 2 µl of DNase (Ambion 2 U/µl). Prior to incubation of cells on the array, the printed area was blocked for 3 minutes with 1% BSA in PBS solution. The blocking solution was replaced by the cell suspension, and the arrays were incubated for 1 hour at 37° C. Excess cells were removed in a large volume of PBS and the arrays were fixed in 4% paraformaldehyde solution for 10 minutes. Cells on the array were permeabilized in 0.2% triton X-100 solution for 20 min, washed twice with PBS and blocked for 45 min in blocking buffer (2% FBS, 2% BSA, 50 mM glycine in PBS). After blocking, arrays were washed twice with PBS and incubated for 2 hours at room temp in working buffer (1:10 diluted blocking buffer added 0.1% of triton) containing the primary antibodies: guinea-pig anti-insulin (DAKO, A0564), rabbit anti-glucagon (DAKO, A0565) and goat anti-somatostatin (Santa Cruz biotechnology, SC-7819) antibodies. Primary antibodies were removed and the arrays were washed three times with working buffer. Then, secondary antibodies were added in working buffer for a 45 min incubation period at room temp: cy5 donkey anti-guinea-pig (Jackson ImmunoResearch 706-175-148), AlexaFluor 488 donkey anti-rabbit (Jackson ImmunoResearch, 711-545-152), cy3 donkey anti-goat (Jackson ImmunoResearch 705-165-147). After the incubation period, arrays were washed three times in working buffer and imaged using automated, high content fluorescence microscopy (IXmicro, MDC). Statistics: P-values of gene expression differences (FIG. 1C; FIG. 2B) were computed using two-sample Paired t-test (one-tail) with equal variances. Number of repeats (n) represents biological replicates using samples derived from different donors.

Cell Sorting Methods

Flow Cytometry:

Cells were dissociated using TrypLE™ Express (Invitrogen 12604) for 4 min, followed by quenching with 10% FBS in PBS. Blocking was performed in 10% FBS in PBS for 45 min on ice. Staining of cells was carried out in PBS containing 3% FBS using the following antibodies (BD biosciences): mouse anti-human CD44 (555476), mouse anti-human CD49B (555497), mouse anti-human EGFR (555996), mouse anti-human CD9 (555370), FITC mouse anti-human CD9 (312104), mouse anti-human CD56 (555514), APC mouse anti-human CD56 (555518), F(ab')2 donkey anti-mouse PE (eBiosciences 12-4012-87) and Alexa Fluor 647. Thresholds were determined using goat anti-mouse IgG1 k isotype control (eBioscience 14-4714-81) as follows: we defined gating that includes over 99% of the IgG control data and set the threshold to 1 log 10 above the boundary of this gate. Propidium iodide (Biotium 40016) was used at 2 µg/ml to mark dead cells. Suspended cells were filtered through 40 µm nylon strainer (BD Falcon), and analyzed/sorted by FACSAria flow cytometer (BD). Intracellular labeling for FACS analysis was performed immediately after the extracellular labeling procedure described above. Cells were fixed and permeabilized in Cytofix/Cytoperm™ solution (BD biosciences 554722) for 1 hour on ice. All washes and subsequent incubations were carried out in Perm/Wash™ buffer (BD biosciences 554723). The following reagents were also used: guinea-pig anti-insulin antibody (DAKO A0564) diluted 1:200, mouse anti-glucagon (abcam, ab10988) diluted 1:200 and goat anti-somatostatin (Santa Cruz biotechnology, SC-7819) diluted 1:1000, for primary antibodies and cy5 donkey anti-guinea-pig (Jackson ImmunoResearch 706-175-148), cy3 donkey anti-mouse (eBiosciences, 12-4012-87) and cy3 donkey anti-goat (Jackson ImmunoResearch 705-165-147) diluted 1:200 for secondary antibody.

Cell Preparation:

Flow cytometry isolated populations were seeded onto the array in a total concentration of ~5*10$^6$ cells/ml in 250-500 µl of hESC growth medium, supplemented with 1 µl of DNase (Ambion 2 U/µl). Prior to incubation of cells on the array, the printed area was blocked for 3 minutes with 1% BSA in PBS solution. The blocking solution was replaced by the cell suspension, and the arrays were incubated for 1 hour at 37° C. Excess cells were removed in a large volume of PBS and the arrays were fixed in 4% paraformaldehyde solution for 10 minutes. Arrays were imaged using automated, high content fluorescence microscopy (IXmicro, MDC).

Real-Time Quantitative PCR:

RNA from sorted populations of cells was isolated using RNeasy MinElute Cleanup kit (Qiagen 74204). DNA was eliminated using TURBO DNA-free kit (Ambion AM1907) and the mRNA was converted to cDNA using high-capacity cDNA Reverse Transcription kit (Ambion 4374967). Transcript levels were measured using real-time qPCR on a 7900HT Fast Real-Time PCR System using Power SYBR green PCR master mix (Applied Biosystems). The levels of each gene was normalized using RPLPO as an endogenous control mRNA. Primer sequences are detailed in Table 1.

TABLE 1

Primers used for PCR

| Gene | Forward primer | SEQ ID # | Reverse primer | SEQ ID # |
|---|---|---|---|---|
| Insulin | GGGGAACGAGGCTTCTTCTAC | 1 | CACAATGCCACGCTTCTGG | 2 |
| Glucagon | GTGCAGTGGTTGATGAATACCAA | 3 | GTCTCTCAAATTCATCGTGACGTT | 4 |
| Somatostatin | CCCCAGACTCCGTCAGTTTC | 5 | CCGTCTGGTTGGGTTCAGA | 6 |
| Trypsin | GCTACAAGTCCCGCATCCA | 7 | TCCCCTCCAGGACTTCGAT | 8 |
| CD9 | CTGCCCCAAGAAGGACGTACT | 9 | CACTGCGCCGATGATGTG | 10 |
| EGFR | TCCAGTGGCGGGACATAGTC | 11 | TTTGGTCAGTTTCTGGCAGTTCT | 12 |
| CD44 | CCTTTGATGGACCAATTACCATAAC | 13 | TCAGGATTCGTTCTGTATTCTCCTT | 14 |
| CD49B | CAGGGCACTATCCGCACAA | 15 | TGTGACCAGAGTTGAACCACTTG | 16 |
| CD56 | GCCAACCCCACAGGAGTTC | 17 | AGCGATAAGTGCCCTCATCTG | 18 |

The following examples are intended to illustrate how to make and use the methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Example 1

The Functional Cell-Capture Screen (FCCS)

An iterative high throughput screen which identifies cell surface markers associated with cell type-specific functionality was developed (FIG. 1A). The analysis is performed in 3 steps which can be iterated to refine the identification of markers for the desired cells. In the first step, a heterogeneous sample is dissociated into single cell suspension and seeded on a glass slide printed with 231 different antibodies against cell-surface marker antigens (each antibody spot is represented in 5 replicates). Since the capture of cells on the array is based on recognition of antigens by the printed antibodies, the populated spots provide a list of cell surface markers expressed by the ensemble of cells in the heterogeneous sample. Each marker may be expressed by one or more cell types within the sample. To determine the association between the identified markers and a desired cell type, the cells on the array are immunostained with antibodies marking cell type-specific functionality (Step 2). Analysis is performed by imaging the arrays with automated, high content fluorescence microscopy (ImageXpress Micro) and calculating for each spot the fraction of cells positive for the relevant functional label. Spots enriched with labeled cells define candidate surface markers for enrichment of cells with the desired functionality. In step 3, cells are FACS sorted using these markers and validate cell type-specific enrichment by measuring expression levels of relevant functional genes. To further refine the enrichment, the entire 3-step procedure is repeated with cells that were sorted using the validated markers.

Example 2

Identification of Cell-Surface Markers in Human Islets of Langerhans

Figure 1B:
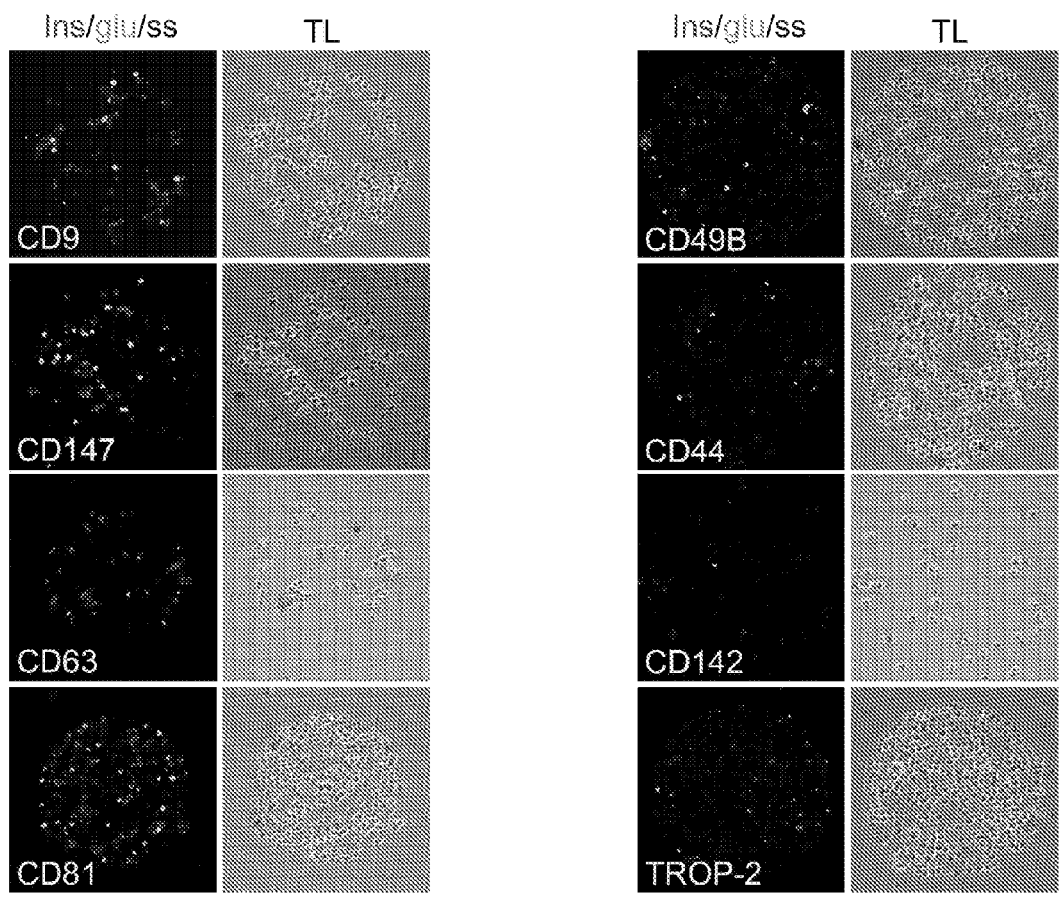
FIG. 1B: Representative images of populated antibody spots with different enrichments of insulin-(Ins), glucagon-(glu) and somatostatin-positive cells (ss). On the right are spots mostly populated by non-endocrine cells, and on the left are spots populated by different proportions of alpha, beta and delta cells. Corresponding phase contrast images are shown on the right of each image. 10× magnification.

The efficiency of the FCCS approach was demonstrated for identification and isolation of insulin-producing beta cells from islet of Langerhans obtained from pancreata of human cadavers. Three independent antibody array analyses of human islets were performed using an antibody procedure described above. This approach proved to be very reliable and effective; despite differences in donor age, gender, BMI and general condition of the islets, more than 60 markers were identified: the majority of the markers were detected in at least two of the three donors. This is particularly significant considering the large heterogeneity in gene expression typically measured by qPCR in human islets derived from different donors (Bar et al., Diabetes. 2008, 57, 2413-2420). Analysis of binding to the antibody array, applied to samples from different islet donors, identified 22 surface markers that were reproducibly expressed in all three donor samples tested (Table 2) Immunostaining of the captured cells for insulin, glucagon and somatostatin (FIG. 1B), revealed a heterogeneous labeling pattern: some of the populated spots, such as CD44 and CD142, were largely unlabeled, representing cell surface markers that are mostly expressed by non-endocrine cells. Other spots showed a much higher percentage of labeled cells indicating efficient capture of endocrine cells (e.g. CD9, CD81, CD147 etc.). These spots represent cell surface markers expressed by alpha, beta and delta cells. Since none of the spots was populated exclusively by insulin, glucagon or somatostatin labeled cells, the newly identified markers were used as a starting point for a second iteration of the FCCS platform. Flow cytometry was used to analyze the relative abundance of cells expressing the identified markers in islet samples from three donors. Some of the markers were expressed by all cells, some in discrete subsets of cells, and yet others exhibited a wide range of expression.

The cell surface marker profile of human islets of Langerhans, provided herein in Table 2, has never before been reported. The table demonstrates marker distribution between different donors as measured by the array. Any of these markers, alone or in combination with other markers could be used to enrich for specific cell types within human islets of Langerhans.

TABLE 2

Summary of results from 3 independent antibody array analyses of human islets of Langerhans, listing cell-surface markers detected in one or more donors.

| Markers detected in 3 donors | Markers detected in 2 donors | Markers detected in 1 donor |
|---|---|---|
| CD147 | CD59 | CD221 3b7 |
| CD49F | CD55 | CLIP |
| CD42B | CD98 | CD28 |
| TROP-2 | BLD groupA | P-Glycoprotein |
| CD197 | CD53 | HLA-A2 |
| CD44 | CD29 | Hematopoietic progenitor cell |
| CD49E | CD99 | CD66C |
| CD15 | CD61 | |
| EGFR | C-ERB-2 | CD226 |
| CD71 | CD3 | CD66B |
| CD36 | B2-microglobulin | CD50 |
| CD177 | CD66 | CD55 |
| CD57 | CD90 | LTBR |
| HLA-ABC | CXCR4 | CD271 |
| CD140B | CD54 | CD45RB |
| CD142 | CD146 | CD164 |
| CD81 | | CD11B/MAC1 |
| CD63 | | HLA-DR |
| CD49B | | CD282 |
| KS1/4 | | CD97 |
| CD47 | | CD11C |
| CD9 | | CD166 |

Subset-specific markers and markers with a broad range of expression were further tested for being useful to enrich for distinct sub-populations and for fractionation of islet samples into distinct cell types.

Example 3

Fractionation of Islet Cells Using the Newly Identified Markers

To prioritize markers for the second iteration, the performance of several markers that were identified in the first iteration was examined. The respective cells were isolated by flow cytometry. In each sub-population, the mRNA expression level of insulin (beta cells), glucagon (alpha cells), somatostatin (delta cells) and trypsin (acinar cells) was compared to that of unsorted (bulk) cells. Of the tested cases, markers that enrich for specific cell types were identified. In particular, cells expressing high levels of CD9 (top 10%) also exhibited higher mRNA levels of insulin and somatostatin, indicating enrichment for beta and delta cells, respectively (FIG. 1C). In contrast, CD44+, CD49B+ and EGFR+ cells had elevated mRNA levels of trypsin, indicating enrichment for acinar cells. The inverse fractions of these populations also enriched for specific cell-types, as indicated for example by elevated glucagon expression in EGFR− cells, suggesting enrichment for alpha cells. These results demonstrate the efficiency of this functional platform for rapid identification of relevant marker combinations in a single experiment.

To test whether combinations of antibodies improve the enrichment of beta cells, the CD9+ compartment was fractionated into EGFR positive and negative subsets and measured the expression of the cell-type specific markers in CD9+/EGFR−, CD9+/EGFR+, CD9−/EGFR−, and CD9−/EGFR+ cells. The combinations of CD9+/EGFR− and CD9−/EGFR− indeed reproducibly improved the enrichment of beta and alpha cells as determined by increased levels of mRNA for insulin and glucagon, respectively. The increased expression of insulin in the CD9+/EGFR− subset was nonetheless accompanied by elevated levels of somatostatin, indicating that the combination of CD9+ and EGFR− is characteristic of both beta and delta cells and does not completely distinguish beta from delta cells. On the other hand, the EGFR−/CD9− combination led to a significant enrichment of alpha cells that could not have been anticipated based on analysis of CD9 and EGFR alone. The enrichment for exocrine cells (CD9−/EGFR+) was also improved compared to the individual sorts with CD9 and EGFR. Taken together, this data suggests that the newly identified markers, particularly CD9 and EGFR are useful for isolating functionally distinct islet sub-populations.

Example 4

Screening for Marker Combinations that Enrich for Insulin-Producing Cells

The purification of beta cells was refined by re-applying the FCCS procedure using $CD9^{high}$ cells (top 10%) isolated by FACS, as the input sample. Markers that are co-expressed with CD9 were identified by capturing $CD9^{high}$ cells on the antibody array, and using immunostaining to screen for spots enriching for insulin and somatostatin positive cells. Nineteen surface markers that were co-expressed with CD9 in two independent experiments were identified (Table 3). Two of these, CD73 and CD56, corresponded to antibody spots that reproducibly enriched for cells exhibiting high levels of insulin staining (FIG. 2A). Despite the relatively low abundance of delta cells in islet samples, somatostatin positive cells were detected in both CD73 and CD56 spots indicating co-enrichment of delta cells in addition to beta cells. Another potentially attractive marker which appeared to enrich for insulin positive cells is the receptor for insulin-like growth factor 1 (CD221, IGF1R). This marker might be used to experimentally manipulate the cells (e.g. inducing selective proliferation using the cognate ligand).

TABLE 3

Cell-surface markers expressed by $CD9^{high}$ cells as detected by the second iteration of the antibody array using functional cell-capture screen (FCCS).

| Marker | Annotation | Symbol | Exemplary Accession no. |
|---|---|---|---|
| CD56 | neural cell adhesion molecule 1 | NCAM1 | NP_000606.3 |
| CD73 | 5′-nucleotidase, ecto | NT5E | NP_001191742.1 |
| CD221 | insulin-like growth factor 1 receptor | IGF1R | NP_000866.1 |
| CD4 | CD4 molecule | CD4 | NP_000607.1 |

TABLE 3-continued

Cell-surface markers expressed by CD9$^{high}$ cells as detected by the second iteration of the antibody array using functional cell-capture screen (FCCS).

| Marker | Annotation | Symbol | Exemplary Accession no. |
|---|---|---|---|
| CD87 | plasminogen activator, urokinase receptor | PLAUR | NP_002650.1 |
| CCR4 | C-C chemokine receptor type 4 | CD194 | NP_005499.1 |
| CD165 | apolipoprotein E | AD2/APOE | Gene ID 23449 |
| CD85J | leukocyte immunoglobulin-like receptor, subfamily B | LILRB1 | NP_001075106.1 |
| CD153 (CD30L) | tumor necrosis factor (ligand) superfamily, member 8 | CD153 | NP_001235.1 |
| CD142 | coagulation factor III (thromboplastin, tissue factor) | F3 | NP_001171567.1 |
| CD134 | Tumor necrosis factor receptor superfamily, member 4 | TNFRSF4 | NP_003318.1 |
| ITGB7 | Integrin, beta 7 | ITGB7 | NP_000880.1 |
| CD68 | CD68 molecule | CD68 | NP_001035148.1 |
| WNT16 | wingless-type MMTV integration site family, member 16 | WNT16 | NP_057171.2 |
| CD18 | integrin, beta 2 (complement component 3 receptor 3 and 4 subunit) | ITGB2 | NP_000202.2 |
| CD6 | CD6 molecule | CD6 | NP_001241679.1 |
| CD77 | alpha 1,4-galactosyltransferase | A4GALT | NP_059132.1 |
| CD61 | integrin, beta 3 (platelet glycoprotein IIIa) | ITGB3 | NP_000203.2 |
| CD32 | Fc fragment of IgG, low affinity IIa, receptor | FCGR2A | NP_001002273.1 |

The results are summary of two independent FCCS analyses of CD9$^+$ cells from two donors.

Example 5

Isolation of Beta Cells Using CD9/CD56 Marker Combination

The new marker combinations were further evaluated by flow cytometry followed by qPCR analysis of isolated subsets. The CD9 high/CD56+ compartment was significantly larger than the CD9$^{high}$/CD73+ fraction indicating that CD56/CD9 based isolation can yield much larger numbers of cells.

To determine if the CD9/CD56 marker combination is capable of generating a purer population of beta cells, different compartments of the islet samples were FACS-isolated based on the expression of CD9 and CD56. In each of the sorted subsets (CD9high/CD56+, CD9$^{high}$/CD56−, CD9−/CD56+ and CD9−/CD56−) the mRNA levels of cell-type specific markers were measured. These levels confirmed the results of the functional assay; CD9$^{high}$/CD56+ cells exhibited significantly higher levels of insulin and somatostatin compared with cells from all other fractions (FIG. 2B), indicating enrichment of beta and delta cells. On the other hand, CD9−/CD56+ and CD9−/CD56− cells exhibited much higher levels of glucagon and trypsin corresponding, respectively, to enrichment of alpha and acinar cells (FIG. 2B).

To evaluate co-occurrence of CD9 and CD56 with insulin on a single cell basis, islet cells that were isolated based on different combinations of CD9 and CD56 expression were immunostained for insulin and somatostatin. Insulin labeling was restricted to the CD9high/CD56+ compartment. Flow cytometry was then used to analyze extracellular labeling of CD9 and CD56 together with intracellular labeling of insulin. It was found that high levels of insulin are restricted to the CD9$^{high}$/CD56+ compartment which further support the capacity of these markers for reproducible purification of beta cells.

Figure 3A:
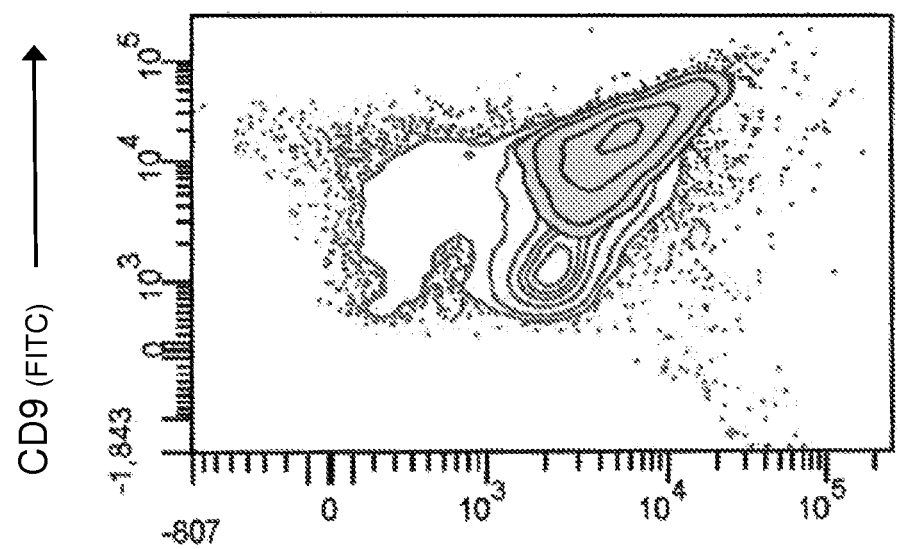
FIG. 3A: The second iteration of FCCS improves the purity and allows increased yield of isolated cells. Top: FACS analysis of CD9 and CD56 expression in islets samples. Overlaid in gray is intracellular staining for insulin demonstrating the co-localization of insulin with $CD9^{high}$/CD56+ expressing cells. Bottom: histogram of all cells vs. the insulin+ population (–intermediate gray) and top 20% of the population by CD9+/CD56+ gating (dark gray). Dashed line indicates the gate for top 10% of the population by CD9 expression. This demonstrates the potential of the CD9/CD56 combination to identify more relevant cells as compared to only CD9. Cells that are not labeled for insulin are shown in light gray.
Figure 3A:
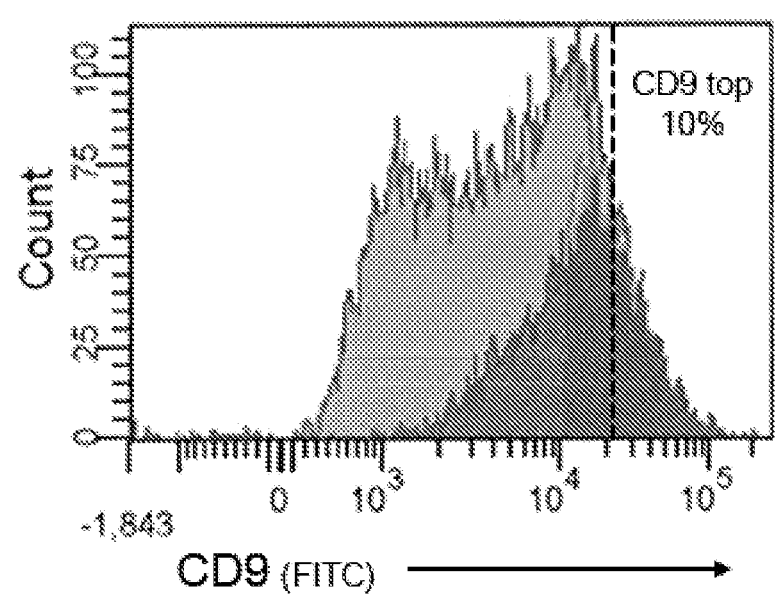
Figure 4:
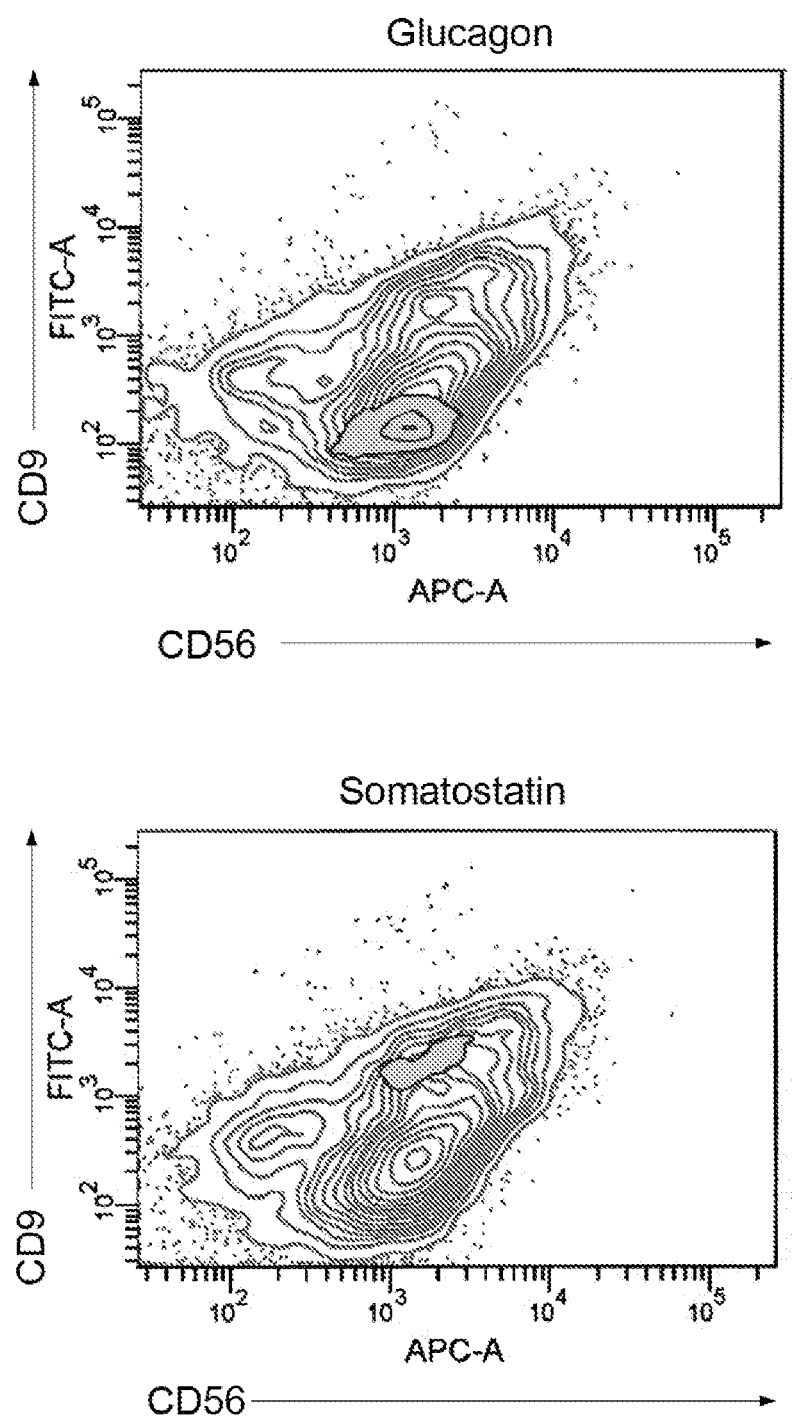
FIG. 4: Alpha and delta cells are restricted to the CD9−/CD56+ and CD9+/CD56+ compartments, respectively. FACS analysis of CD9 and CD56 expression in islets samples. Overlaid filled in gray is intracellular staining for glucagon (top) or somatostatin (bottom).

Simultaneous extracellular and intracellular FACS analysis is currently the only method allowing rigorous measurements of both purity and yield. We thus performed triple staining of islet cells with CD9, CD56 and insulin antibodies, followed by simultaneous intra- and extracellular FACS analysis, showed that insulin labeling was restricted to the CD9$^{high}$/CD56+ compartment (FIG. 3A). Similar intracellular FACS analysis for glucagon and somatostatin (instead of insulin) showed that glucagon+ alpha cells localize to the CD9−/CD56+ compartment while somatostatin+ delta cells are restricted to the CD9$^{high}$/CD56+ fraction (FIG. 4).

Figure 3B:
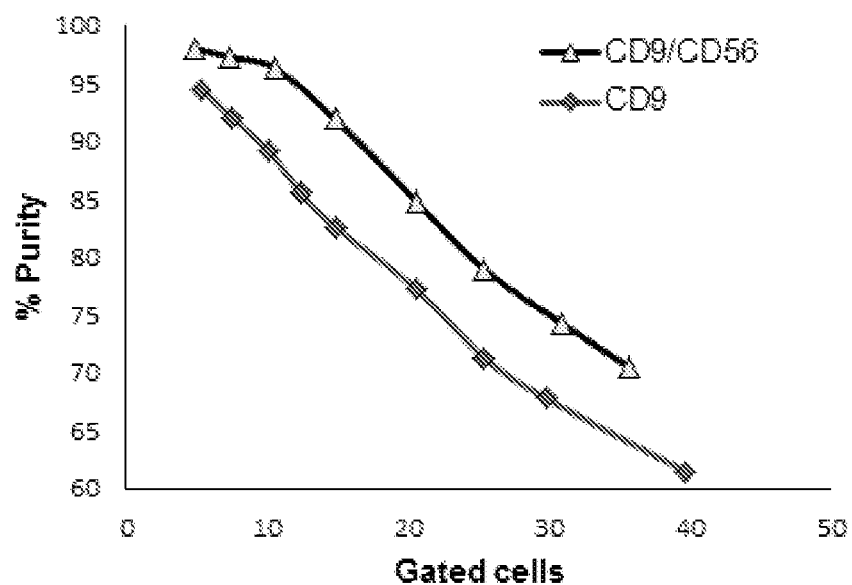
FIG. 3B: The second iteration of FCCS improves the purity and allows increased yield of isolated cells. Top: comparison of purity (% of insulin+ cells in the isolated fraction) obtained by CD9/CD56 based isolation and CD9 based isolation at different choices of gating. Bottom: comparison of CD9/CD56-based and CD9-based isolation with respect to beta cell yield (fraction of insulin+ cells out of total beta cells) and purity. The yield is calculated based on the same gates as the purity.
Figure 3B:
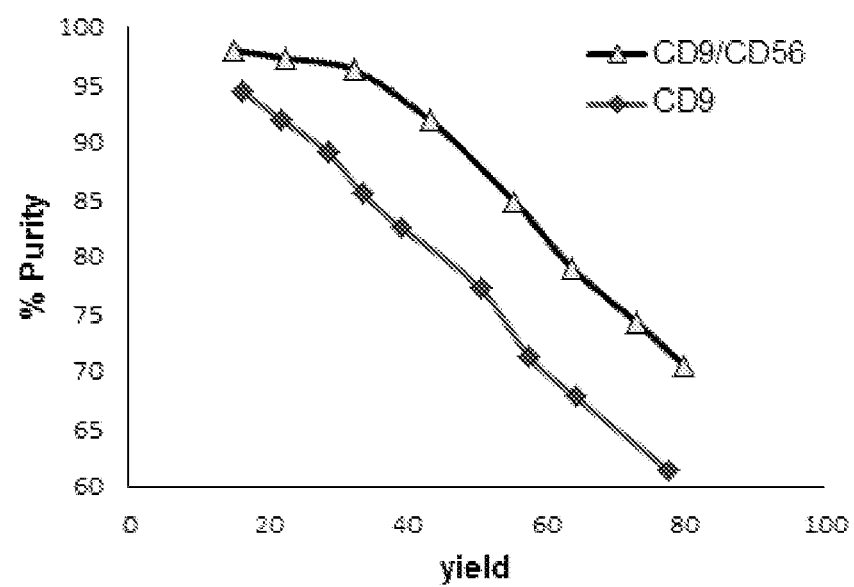

To evaluate the added value of the second iteration, the purity and yield of beta cells isolated based on the CD9/CD56 combination were compared to isolation based on CD9 alone. The proportion of beta cells was analyzed using a series of different gating options from very stringent to very permissive. While both single and double marker isolation schemes could achieve high cell purity, the CD9/CD56 based isolation outperformed the CD9 based isolation at all choices of gating (Table 4, FIG. 3B). Increasing CD9 gating over 10% introduces considerable non-beta cell contamination to the isolated compartment. Using the CD9/CD56 combination eliminates much of this undesired fraction and allows a significant increase in beta cell yield under permissive gating, without compromising purity (FIGS. 3A and 3B). Gating stringency of CD9 and CD56 may be thus used to control and adapt purity and yield for different applications. Improved purity often comes at the expense of yield. Consequently, addition of a second marker for isolation tends to restrict the selection, resulting in reduced yield. Nevertheless, the iterative use of the FCCS allowed us to identify a combination of markers (CD9 and CD56) which increased the purity without compromising the yield. This confirms that cell type-specific enrichment can be enhanced by iterating the FCCS procedure. The capacity of the FCCS approach to identify relevant markers for enrichment of specific cell types from a limited, heterogeneous and fluctuating cellular context was also demonstrated.

TABLE 4

Values of purity and yield for different gating of CD9 and CD9/CD56

| % CD9/CD56 | β cell Purity (%) | Yield (% of β cells) |
|---|---|---|
| 5 | 98 | 15 |
| 10 | 96 | 32 |
| 20 | 85 | 55 |

TABLE 4-continued

Values of purity and yield for different gating of CD9 and CD9/CD56

| | β cell Purity (%) | Yield (% of β cells) |
|---|---|---|
| 30 | 74 | 73 |
| 35 | 71 | 80 |
| % CD9 | | |
| 5 | 94 | 16 |
| 10 | 89 | 29 |
| 20 | 77 | 51 |
| 30 | 68 | 64 |
| 40 | 61 | 78 |

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. A method of isolating an enriched population of at least one distinct type of pancreatic cells from cells of human adult islets of Langerhans, the method comprising sorting the cells using a combination of at least two cell-surface markers relevant to the cell type to be isolated, wherein the at least one distinct type of cells is selected from the group consisting of: beta cells and delta cells, and wherein one of the at least two cell-surface markers is CD9 and the cell isolation is for an enriched population of cells expressing high levels of the cell-surface marker CD9.

2. The method of claim 1, wherein said sorting using said combination of at least two cell-surface markers is effected sequentially and the cell-surface marker CD9 is the first marker used for isolation.

3. The method of claim 1, further comprising the steps of:
  i. obtaining said cells of human adult islets of Langerhans from recovered or extracted pancreatic tissue;
  ii. exposing the cells obtained in (i) to a probe capable of identifying CD9+ cells and to at least one additional probe; and
  iii. isolating cells expressing CD9 and the additional probe by sorting of cells, thereby isolating an enriched population of at least one distinct cell type selected from the group consisting of: beta cells and delta cells.

4. The method of claim 1, wherein the cells are isolated using a combination of CD9 and at least one cell-surface marker selected from the group consisting of: CD56, EGFR, CD4, CD73, CD87, CCR4, CD165, CD85J, CD221, CD153 (CD30L), CD142, CD134, ITGB7, CD68, WNT16, CD18−, CD6, CD77−, CD61, and CD32.

5. The method of claim 1, wherein said sorting is performed with anti CD9 and anti CD56 antibodies, wherein said anti-CD9 and said anti-CD56 are used for positive selection.

6. The method of claim 1, wherein said sorting is performed with anti-CD9 and anti-EGFR antibodies, wherein said anti-CD9 is used for positive selection and said anti-EGFR is used for negative selection.

7. The method of claim 3, wherein the at least one additional probe is capable of identifying a cell-surface marker selected from the group consisting of: CD4 (NP_000607.1), CD73 (NP_001191742.1, CD87 (NP_002650.1), CCR4 (NP_005499.1), CD165 (Gene ID 23449), CD85J (NP_001075106.1), CD221 (NP_000866.1), CD153 (CD30L) (NP_001235.1), CD142 (NP_001171567.1), CD134 (NP_003318.1), ITGB7 (NP_000880.1), CD68 (NP_001035148.1), WNT16 (NP_057171.2), CD18 (NP_000202.2), CD6 (NP_001241679.1), CD77 (NP_059132.1), CD61 (NP_000203.2), and CD32 (NP_001002273.1).

8. The method of claim 3, wherein the enriched cells of the population of at least one distinct cell type selected from the group consisting of: beta cells and delta cells are subject to additional iterations of steps (ii)-(iii).

9. The method of claim 3, wherein the sorting of the enriched cells of the population of at least one distinct cell type selected from the group consisting of: beta cells and delta cells (iii) is performed via fluorescence activated cell sorting (FACS).

10. A method for identifying cell-surface marker combinations suitable of purifying an enriched population of insulin-producing beta cells within pancreatic tissue, the method comprising the steps of:
  i. obtaining a heterogeneous population of cells selected from a group consisting of cells recovered or extracted from pancreatic tissue, committed lineages of stem cells and cultures of differentiated stem cells;
  ii. isolating CD9+ cells from the cells obtained in (i);
  iii. applying the CD9+ cells of (ii) to an array comprising antibodies against cell-surface markers, wherein said antibodies are attached on said array;
  iv. fixing, permeabilizing and immunostaining the bound cells of (iii) with antibodies against insulin, thereby identifying antibody stained loci enriched for beta cells; and
  v. determining the cell-surface markers of the loci enriched for beta cells in (iv).

11. The method of claim 10, wherein the heterogeneous population of cells comprises one or more of pancreatic exocrine cells, pancreatic endocrine cells and non-pancreatic cells.

12. A method of isolating at least one distinct type of cells from a heterogeneous population of cells recovered or extracted from pancreatic tissue, the method comprising sorting the cells using a combination of cell-surface markers CD9 and CD56, wherein the at least one distinct type of cells is selected from the group consisting of: insulin-secreting beta cells or beta cell progenitors, somatostatin-secreting delta cells, glucagon secreting alpha cells and trypsin-secreting exocrine cells.

13. The method of claim 12, wherein glucagon-secreting alpha cells are isolated using a combination of the cell-surface markers CD9 and CD56, wherein the CD9 marker is used for negative selection and the CD56 marker is used for positive selection.

14. The method of claim 12 wherein trypsin-secreting acinar cells are isolated using a combination of the cell surface markers CD9 and CD56, wherein both markers are used for negative selection.

15. The method of claim 12, wherein said sorting is performed with anti CD9 and anti CD56 antibodies, wherein said anti-CD9 and said anti-CD56 are used for positive selection.

16. The method of claim 12, wherein the heterogeneous population of cells is selected from the group consisting of cells recovered or extracted from pancreatic tissue, committed lineages of stem cells and cultures of differentiated stem cells.

17. A method of isolating at least one distinct type of cells from a heterogeneous population of cells recovered or extracted from pancreatic tissue, the method comprising sorting the cells using a combination of cell-surface markers CD9 and EGFR, wherein the at least one distinct type of cells is selected from the group consisting of: insulin-secreting beta cells or beta cell progenitors, somatostatin-secreting delta cells, glucagon secreting alpha cells and trypsin-secreting exocrine cells.

18. The method of claim 17, wherein said sorting is performed with anti CD9 and anti EGFR antibodies, wherein said anti-CD9 is used for a positive selection and wherein said anti EGFR is used for a negative selection.

19. The method of claim 17, wherein the heterogeneous population of cells is selected from the group consisting of cells recovered or extracted from pancreatic tissue, committed lineages of stem cells and cultures of differentiated stem cells.

20. The method of claim 17, wherein said sorting is performed with anti CD9 and antibody selected from the group consisting of anti CD49B, anti EGFR and anti CD44, wherein said anti CD9 is for negative selection and wherein each of said anti CD49B, anti EGFR and anti CD44 is for positive selection.

21. A method of isolating at least one distinct type of cells from a heterogeneous population of cells recovered or extracted from pancreatic tissue, the method comprising sorting the cells using a combination of at least the following cell-surface markers selected from the group consisting of:
(i) CD9 and CD73,
(ii) CD9 and CD221,
(iii) CD9 and CD81,
(iv) CD9 and CD147,
(v) CD9 and CD49B,
(vi) CD9 and CD44,
(vii) CD9 and CD142,
(viii) CD9 and CD18,
(ix) CD9 and CD134,
(x) CD9 and CD4, and
(xi) CD9 and ITGB7,
wherein the at least one distinct type of cells is selected from the group consisting of: insulin-secreting beta cells or beta cell progenitors, somatostatin-secreting delta cells, glucagon secreting alpha cells and trypsin-secreting exocrine cells.

22. The method of claim 21, wherein said CD9 is for positive selection.

23. The method of claim 21, further comprising sorting the cells using the CD56 cell surface marker.

24. The method of claim 23, wherein said CD56 is for positive selection.

25. The method of claim 21, wherein each of said CD9, said CD73, said CD73, said CD221, said CD81, and said CD147 is for positive selection.

26. The method of claim 21, wherein each of said CD49B, said CD44, said CD142, said CD18, said CD134, said CD4 and said ITGB7 is for negative selection.

27. The method of claim 1, further comprising the steps of:
(a) obtaining said cells of human adult islets of Langerhans from recovered or extracted pancreatic tissue;
(b) exposing the cells obtained in (a) to a probe capable of identifying CD9− cells and to at least one additional probe; and
(c) isolating CD9− cells which express the additional probe by sorting, thereby isolating an enriched population of at least one distinct cell type selected from the group consisting of: alpha cells and exocrine cells.

28. The method of claim 27, wherein when said additional probe is CD56, then the resulting isolated cells are enriched for said alpha cells.

29. The method of claim 27, wherein when said additional probe is selected from the group consisting of EGFR, CD44 and CD49b, then the resulting isolated cells are enriched for said exocrine cells.

30. The method of claim 1, further comprising the steps of:
(a) obtaining said cells of human adult islets of Langerhans from recovered or extracted pancreatic tissue;
(b) exposing the cells obtained in (a) to a probe capable of identifying CD9− cells and to at least one additional probe; and
(c) isolating CD9− cells which do not express the additional probe by sorting, thereby isolating an enriched population of at least one distinct cell type selected from the group consisting of: alpha cells and exocrine cells.

31. The method of claim 30, wherein when said additional probe is CD56, then the resulting isolated cells are enriched for said exocrine cells.

32. The method of claim 30, wherein when said additional probe is selected from the group consisting of: EGFR, CD44 and CD49b, then the resulting isolated cells are enriched for said alpha cells.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: artificial sequence
<220> FEATURE:
<223> OTHER INFORMATION: Primer

<400> SEQUENCE: 1
ggggaacgag gcttcttcta c                                    21

<210> SEQ ID NO 2
<211> LENGTH: 19
<212> TYPE: DNA
<213> ORGANISM: artificial sequnce
<220> FEATURE:
<223> OTHER INFORMATION: Primer

<400> SEQUENCE: 2
cacaatgcca cgcttctgg                                       19

<210> SEQ ID NO 3
<211> LENGTH: 23
<212> TYPE: DNA
<213> ORGANISM: artificial sequence
<220> FEATURE:
<223> OTHER INFORMATION: Primer

<400> SEQUENCE: 3
gtgcagtggt tgatgaatac caa                                  23

<210> SEQ ID NO 4
<211> LENGTH: 24
<212> TYPE: DNA
<213> ORGANISM: artificial sequence
<220> FEATURE:
<223> OTHER INFORMATION: Primer

<400> SEQUENCE: 4
gtctctcaaa ttcatcgtga cgtt                                 24

<210> SEQ ID NO 5
<211> LENGTH: 20
<212> TYPE: DNA
<213> ORGANISM: artificial sequence
<220> FEATURE:
<223> OTHER INFORMATION: Primer

<400> SEQUENCE: 5
```

-continued ccccagactc cgtcagtttc                                              20

<210> SEQ ID NO 6
<211> LENGTH: 19
<212> TYPE: DNA
<213> ORGANISM: artificial sequence
<220> FEATURE:
<223> OTHER INFORMATION: Primer

<400> SEQUENCE: 6
ccgtctggtt gggttcaga                                               19

<210> SEQ ID NO 7
<211> LENGTH: 19
<212> TYPE: DNA
<213> ORGANISM: artificial sequnce
<220> FEATURE:
<223> OTHER INFORMATION: Primer

<400> SEQUENCE: 7
gctacaagtc ccgcatcca                                               19

<210> SEQ ID NO 8
<211> LENGTH: 19
<212> TYPE: DNA
<213> ORGANISM: artificial sequence
<220> FEATURE:
<223> OTHER INFORMATION: Primer

<400> SEQUENCE: 8
tcccctccag gacttcgat                                               19

<210> SEQ ID NO 9
<211> LENGTH: 21
<212> TYPE: DNA
<213> ORGANISM: artificial sequence
<220> FEATURE:
<223> OTHER INFORMATION: Primer

<400> SEQUENCE: 9
ctgccccaag aaggacgtac t                                            21

<210> SEQ ID NO 10
<211> LENGTH: 18
<212> TYPE: DNA
<213> ORGANISM: artificial sequence
<220> FEATURE:
<223> OTHER INFORMATION: Primer

<400> SEQUENCE: 10
cactgcgccg atgatgtg                                                18

<210> SEQ ID NO 11
<211> LENGTH: 20
<212> TYPE: DNA
<213> ORGANISM: artificial sequnce
<220> FEATURE:
<223> OTHER INFORMATION: Primer

<400> SEQUENCE: 11
tccagtggcg ggacatagtc                                              20

<210> SEQ ID NO 12
<211> LENGTH: 23
<212> TYPE: DNA

```
<213> ORGANISM: artificial sequence
<220> FEATURE:
<223> OTHER INFORMATION: Primer

<400> SEQUENCE: 12
tttggtcagt ttctggcagt tct                                              23

<210> SEQ ID NO 13
<211> LENGTH: 25
<212> TYPE: DNA
<213> ORGANISM: artificial sequence
<220> FEATURE:
<223> OTHER INFORMATION: Primer

<400> SEQUENCE: 13
cctttgatgg accaattacc ataac                                            25

<210> SEQ ID NO 14
<211> LENGTH: 25
<212> TYPE: DNA
<213> ORGANISM: artificial sequence
<220> FEATURE:
<223> OTHER INFORMATION: Primer

<400> SEQUENCE: 14
tcaggattcg ttctgtattc tcctt                                            25

<210> SEQ ID NO 15
<211> LENGTH: 19
<212> TYPE: DNA
<213> ORGANISM: artificial sequnce
<220> FEATURE:
<223> OTHER INFORMATION: Primer

<400> SEQUENCE: 15
cagggcacta tccgcacaa                                                   19

<210> SEQ ID NO 16
<211> LENGTH: 23
<212> TYPE: DNA
<213> ORGANISM: artificial sequence
<220> FEATURE:
<223> OTHER INFORMATION: Primer

<400> SEQUENCE: 16
tgtgaccaga gttgaaccac ttg                                              23

<210> SEQ ID NO 17
<211> LENGTH: 19
<212> TYPE: DNA
<213> ORGANISM: artificial sequence
<220> FEATURE:
<223> OTHER INFORMATION: Primer

<400> SEQUENCE: 17
gccaacccca caggagttc                                                   19

<210> SEQ ID NO 18
<211> LENGTH: 21
<212> TYPE: DNA
<213> ORGANISM: artificial sequence
```

```
<220> FEATURE:
<223> OTHER INFORMATION: Primer

<400> SEQUENCE: 18
agcgataagt gccctcatct g                                            21
```